United States Patent
Chen et al.

(10) Patent No.: US 8,444,877 B2
(45) Date of Patent: May 21, 2013

(54) HIGH DIELECTRIC CONSTANT LIQUID CRYSTAL

(75) Inventors: Xinhua Chen, Erie, CO (US); R. Amaranatha Reddy, Boulder, CO (US)

(73) Assignee: VVI Bright China Ltd., Nanjing (CN)

( * ) Notice: Subject to any disclaimer, the term of this patent is extended or adjusted under 35 U.S.C. 154(b) by 0 days.

(21) Appl. No.: 12/812,198

(22) PCT Filed: Jan. 15, 2009

(86) PCT No.: PCT/US2009/031094
§ 371 (c)(1),
(2), (4) Date: Feb. 8, 2011

(87) PCT Pub. No.: WO2009/091884
PCT Pub. Date: Jul. 23, 2009

(65) Prior Publication Data
US 2011/0121232 A1    May 26, 2011

Related U.S. Application Data

(60) Provisional application No. 61/021,552, filed on Jan. 16, 2008.

(51) Int. Cl.
*C09K 19/52* (2006.01)
*C09K 19/06* (2006.01)
*C09K 19/30* (2006.01)
*C07C 19/08* (2006.01)
*C07D 331/02* (2006.01)

(52) U.S. Cl.
USPC ............ 252/299.6; 252/299.01; 252/299.61; 252/299.62; 252/299.63; 428/1.1; 349/1; 349/56; 349/182; 570/127; 570/129; 549/1; 549/200; 532/400; 540/200

(58) Field of Classification Search
USPC ............ 252/299.01, 299.6, 299.61, 299.62, 252/299.63; 428/1.1; 349/1, 56, 182; 570/127, 570/129; 549/1, 200; 532/400; 540/200
See application file for complete search history.

(56) References Cited

U.S. PATENT DOCUMENTS

| | | | |
|---|---|---|---|
| 4,988,701 | A | 1/1991 | Di Domenico et al. |
| 5,474,707 | A | 12/1995 | Takatsu et al. |
| 6,548,126 | B1 | 4/2003 | Sasada et al. |
| 7,052,742 | B1 | 5/2006 | Hornung et al. |
| 7,279,203 | B2 | 10/2007 | Tsuda et al. |
| 7,427,693 | B1 * | 9/2008 | Chen ............... 568/330 |

FOREIGN PATENT DOCUMENTS

| | | |
|---|---|---|
| DE | 43 16 444 A1 | 11/1994 |
| DE | 4316444 A1 * | 11/1994 |
| DE | 196 07 999 A1 | 9/1997 |
| DE | 19607999 A1 * | 9/1997 |
| EP | 0 500 072 A1 | 8/1992 |

* cited by examiner

*Primary Examiner* — Geraldina Visconti
(74) *Attorney, Agent, or Firm* — Lathrop & Gage LLP

(57) ABSTRACT

Provided are liquid crystal compounds and mixtures incorporating the same. The liquid crystal compounds of the invention generally comprise a terminal cyclopentene group, along with at least two other ring groups.

19 Claims, No Drawings

HIGH DIELECTRIC CONSTANT LIQUID CRYSTAL

CROSS-REFERENCE TO RELATED APPLICATIONS

This application is the U.S. National Stage of International Application No. PCT/US2009/031094, filed Jan. 15, 2009, which claims the benefit of U.S. Provisional Application Ser. No. 61/021,552, filed Jan. 16, 2008, both of which are hereby incorporated by reference.

BACKGROUND OF THE INVENTION

Liquid crystal displays use mixtures of liquid crystals having desired material properties such as operating temperature range, thermal stability, light stability, switching time, and contrast ratio. The properties of the mixtures and devices are determined by the constituents of the mixtures.

The demand for liquid crystal displays having improved performance has increased. In particular, liquid crystal mixtures having low threshold voltage are desired, especially for display applications. The threshold voltage is the amount of voltage needed to apply across a pixel to produce a response. Addressing pixels with lower voltages allows simplification of the electronics used, resulting in the possibility for space and weight savings. The threshold voltage is inversely proportional to the dielectric anisotropy of the mixture. Therefore, one way to produce a liquid crystal mixture having a low threshold voltage is the use of mixtures having a large dielectric constant.

German patent application DE4316444A1 (Delavier et al) discloses polymerizable compounds having at one end a chiral 3-oxyalkyl cyclopentene group, where the alkyl group has between 5-20 carbon atoms. U.S. Pat. No. 7,052,742 describes certain five membered ring compounds useful generally in FLC mixtures. German patent application DE 19607999A1 (Kirsch et al) describes certain derivatives of cyclopent-3-en-1-yl.

There is a continuing need in the art for improved liquid crystal compounds and mixtures.

BRIEF SUMMARY OF THE INVENTION

Provided are liquid crystal compounds and mixtures incorporating the same. The liquid crystal compounds of the invention generally comprise a terminal cyclopentene group, along with at least two other ring groups. More specifically, compounds of the invention comprise compounds having the Formula I:

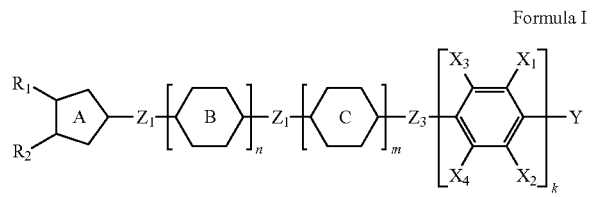

Formula I where

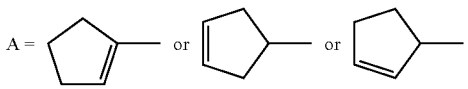

wherein one or more hydrogen atoms on the A ring may be replaced with one or more halogen atoms;

$R^1$ and $R^2$, independently of one another, are selected from the group consisting of: H and unsubstituted or monosubstituted alkyl having 1-12 carbon atoms, wherein the substitution is halogen or CN, wherein one or more $CH_2$ groups of the alkyl group may be independently replaced by —O—, —S—, —CO—, —CO—O—, —O—CO—, —O—CO—O— or —CH=CH—, provided that heteroatoms are not directly connected;

B and C are each independently selected from the group consisting of: 1,4-cyclohexene, cyclohexenyl, 1,4-phenyl, 1,3-dioxan-5,2-diyl, Pyridin-5,2-diyl, pyrimidin-5,2-diyl, naphthalene-2,6-diyl, trans-decahydronaphthalene-2,6-diyl, tetrahydronaphthalene-2,6-diyl, indeneyl, phenanthryl, and dibenzo[b,d]furan; in which one or more hydrogen atoms in any ring structure may be independently replaced by one or more halogen atoms;

Z1 is selected from a single bond or —$(CH_2)_k$—, where k is an integer from 1 to 8 and wherein one or more hydrogen atoms may be replaced by halogen or CN, and one or more $CH_2$ groups may be independently replaced by —O—, —S—, —CO—, —CO—O—, —O—CO—, —O—CO—O—, —CH=CH—, or —C≡C—, provided that heteroatoms are not directly connected;

Z2 and Z3 are each independently selected from the group consisting of: a single bond, —$(CH_2)_2$—, —$(CH_2)_4$—, —CH=CHCH$_2$CH$_2$—, —CH$_2$CH$_2$CH=CH—, CF$_2$O, OCF$_2$, CF$_2$CF$_2$, CF=CF, CH$_2$CF$_2$, CF$_2$CH$_2$, OCF2CF2O, C2H4CF2O, CH$_2$O, OCH$_2$, —CH=CH—, —C≡C—, and COO;

K is 0 or 1;

n and m are independently 0, 1, or 2; wherein K+n+m≧2;

X1, X2, X3 and X4 are independently in each instance selected from the group consisting of: H, F, Cl, CF$_3$, CHF$_2$, and CN;

Y is selected from the group consisting of: H, F, Cl, CN, NCS, OCHF$_2$, CHF$_2$, OCF$_3$, CF$_3$, $C_{1-20}$ alkyl, $C_{1-20}$ alkoxy, $C_{1-20}$ alkenyl, and $C_{1-20}$alkenyloxy wherein one or more hydrogen atoms in the alkyl, alkoxy, alkenyl, alkenyloxy groups may be independently substituted by one or more halogen atoms;

one or more hydrogen atoms in any portion of the Formula may be replaced with deuterium;

provided that the linker between the A ring and the next ring is not —OC(=O)—; —OCH$_2$—; or —CH$_2$CH$_2$— and provided that when A is

the linker between the A ring and the next ring is not —$C_nH_{2n}$O—, where n is 5 to 20; and provided that when A is

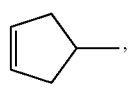

Y is only selected from F, Cl, CN, NCS.

In one embodiment, there are one or more chlorine atoms on one or more A or B rings. In one embodiment, one or more of Z1, Z2 and Z3 contain an even number of carbon atoms. As used herein, a "single bond" as a variable means that there is a direct linkage between two structures. For example, if Z1 is a single bond and n is 1, there is a direct linkage between the A ring and the B ring. In one embodiment, the group between the cyclopentene group and the next ring in the structure contains less than 5 carbon atoms. As used herein, halogen means fluorine, chlorine, bromine or iodine.

In an embodiment, one or more hydrogen atoms on one or more rings is replaced with deuterium. In an embodiment, one or more hydrogen atoms on a non-ring structure is replaced with deuterium.

In separate embodiments, the A ring has the structure:

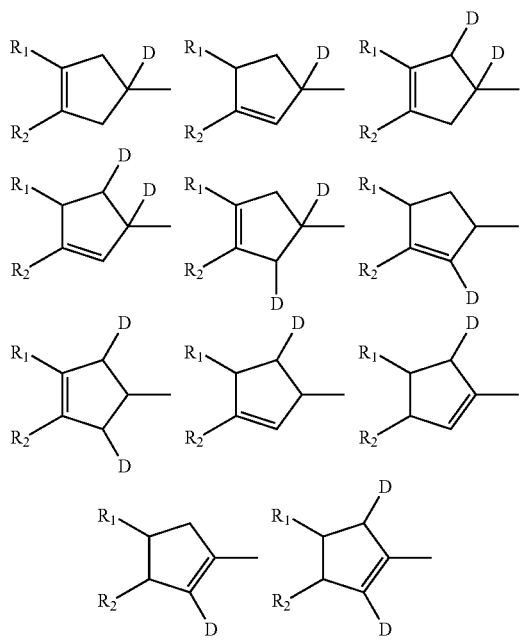

All other possible locations of one or more deuterium substitution for hydrogen in the structures shown herein are intended to be included to the same extent as if they were individually shown.

The description herein provides some additional exemplary embodiments of the invention and variables which can be separate or combined together in all possible permutations, independently and in combination, to formulate compounds of the invention.

The compounds of the invention may have a negative or positive dielectric constant. The use of compounds and mixtures having negative or positive dielectric constants is known in the art. In some embodiments of the invention, the compounds have positive dielectric constant at least 8. In some embodiments of the invention, the compounds have a negative dielectric constant of −2 or less. Larger negative numbers are desired.

Positive Dielectric Constant Compounds

Specific particular embodiments of compounds of the invention having positive dielectric constants are shown below in structures I-1 through I-12. In the structures below, the following definitions apply:

R is C1-C7 n-alkyl;
Y is independently selected from the group consisting of: F, Cl, CF3, OCF3, OCHF2, and OCF2CF3;
X1, X2, X3 and X4 are each, independently of one another, H or F;
Z is independently —C2H4-, —CF2O—, —CF=CF—, —C2F4-, or —CO2-.

It is noted that any of the hydrogen atoms on the cyclopentene ring may be substituted with one or more deuterium atoms.

All possible combinations of positions of the double bond in the cyclopentene ring and the R variables are provided, even if not expressly shown. For example,

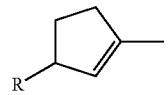

can also be

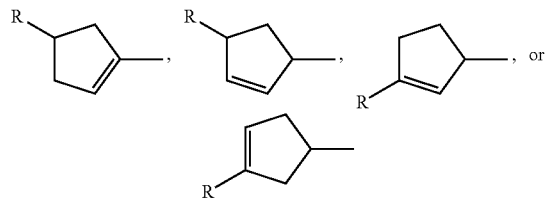

More specific compounds of the invention are shown below:

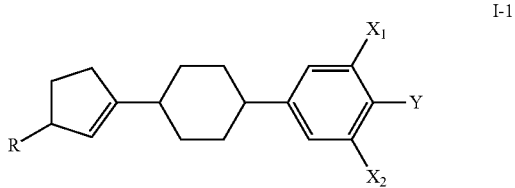

I-1

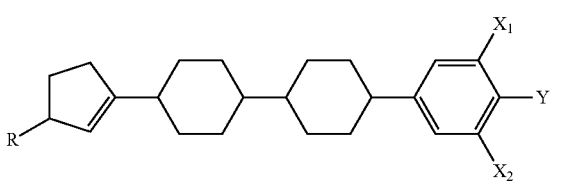

I-2

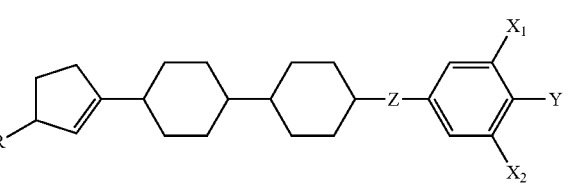

I-3

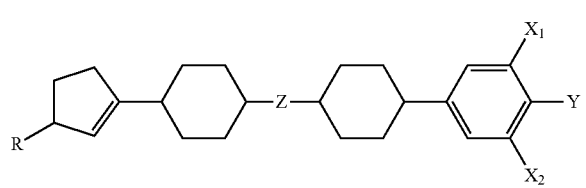

I-4

I-5
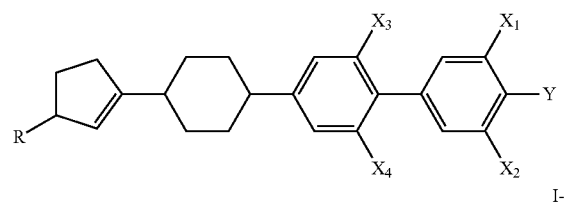

I-6
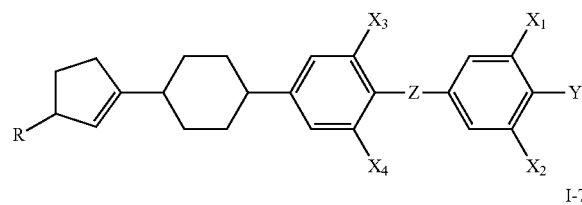

I-7
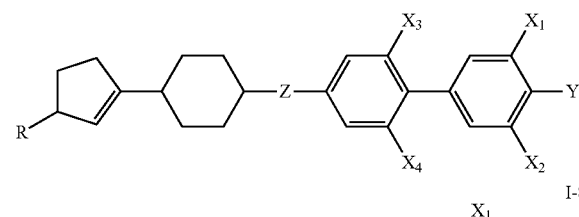

I-8
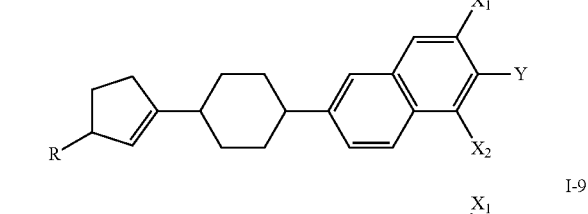

I-9
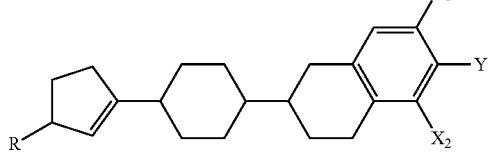

I-10
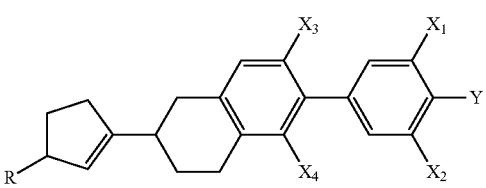

I-11
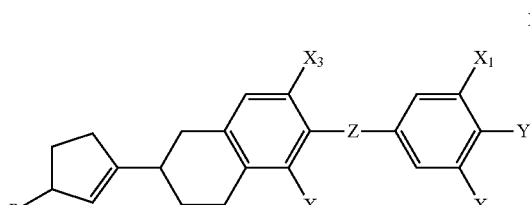

I-12
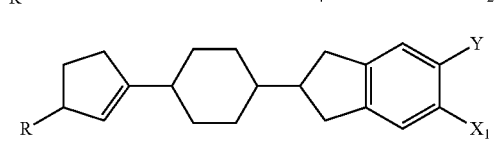

Negative Dielectric Constant Compounds

Specific particular embodiments of compounds of the invention having negative dielectric constants. Some examples of compounds of the invention having negative dielectric constants are shown below in structures I-13 through I-25. In the structures below, the following definitions apply:

R is $C_1$-C7 n-alkyl;

R' is C1-C7 alkyl or alkoxy;

X1, X2, X3 and X4 are independently selected from the group consisting of: H, F, Cl, CHF2 and CF3; with the proviso that at least two of X1 to X4 are independently F, Cl, CHF2 or CF3;

Z is independently selected from the group consisting of: —C2H4-, —CF2O—, —CF=CF—, —C2F4-, and —CO2-.

In separate embodiments, any of the hydrogen atoms on the cyclopentene ring may be substituted with one or more deuterium atoms.

All possible combinations of positions of the double bond in the cyclopentene ring and the R variables are provided, even if not expressly shown. For example,

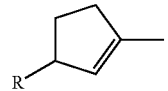

can be also

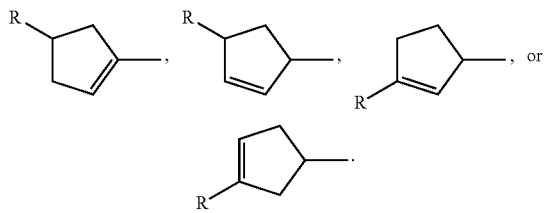

Specific examples of negative dielectric constant compounds of the invention are shown below, in formulas I-13 through I-25:

I-13
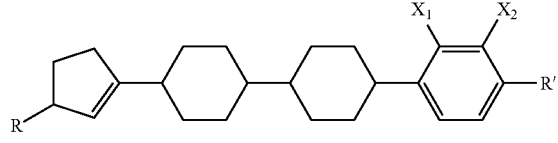

I-14
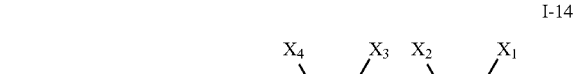

I-15
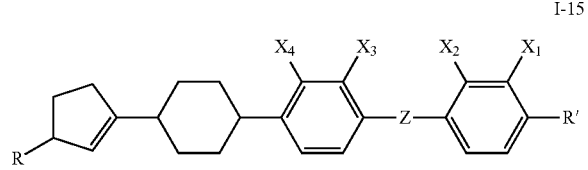

I-16 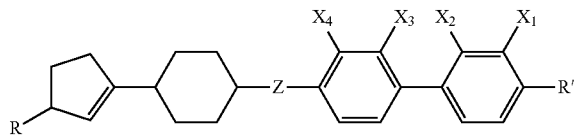

I-17 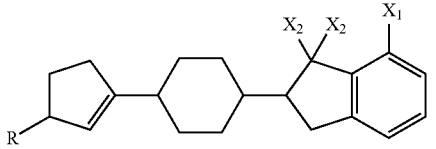

I-18 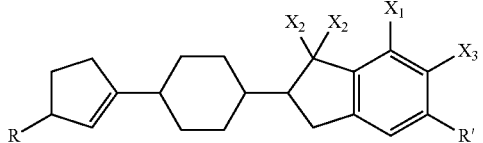

I-19 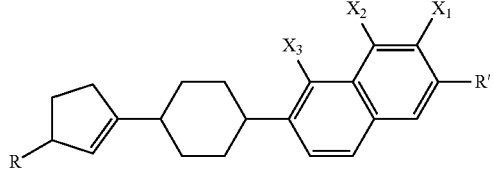

I-20 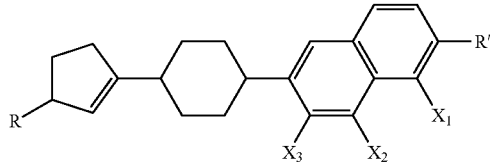

I-21 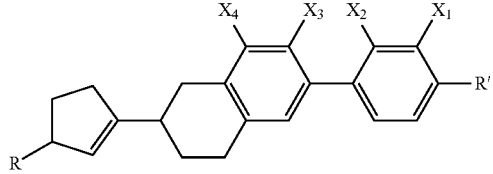

I-22 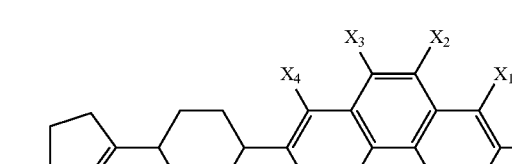

I-23 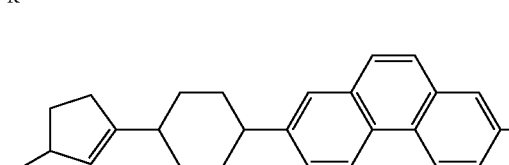

I-24 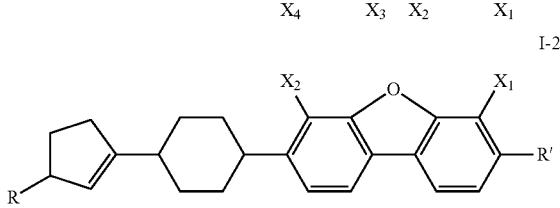

I-25 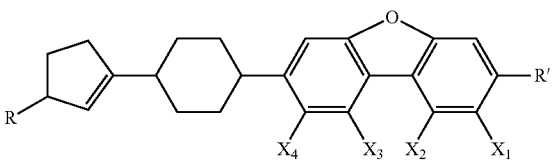

Mixtures

The compounds of the invention may be used as components in any desired liquid crystal mixture, such as those mixtures known in the art. In one embodiment, the liquid crystal mixture having positive dielectric constant comprises one or more compounds of Formula I, such as I-1 to I-12. The mixture may additionally comprise one or more compounds selected from the group consisting of compounds of the general formulae II to XV:

II 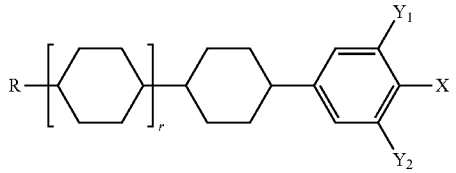

III 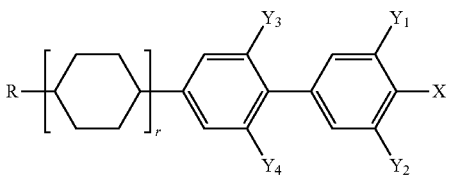

IV 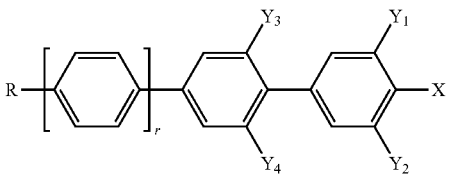

V 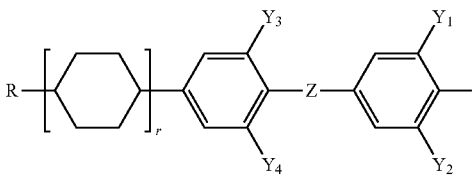

VI 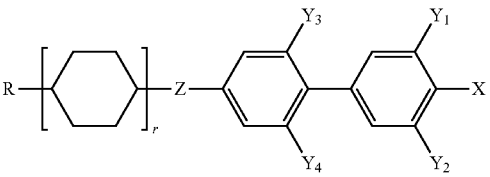

VII 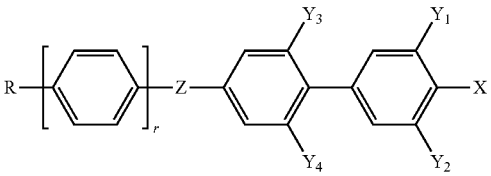

-continued

VIII
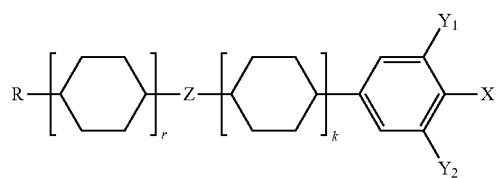

IX
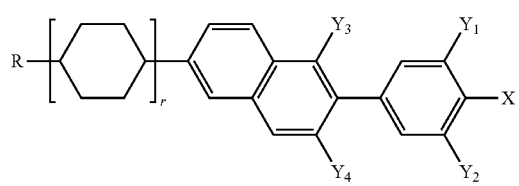

X
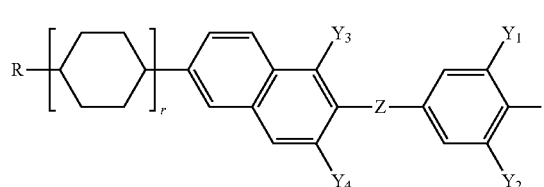

XI
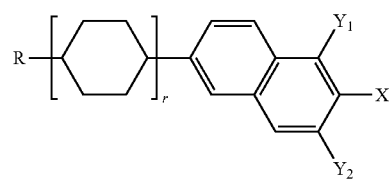

XII
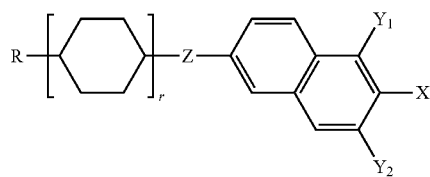

XIII
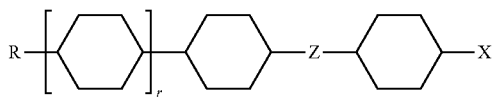

XIV
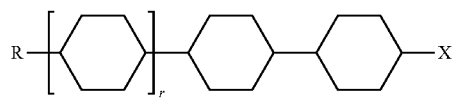

XV
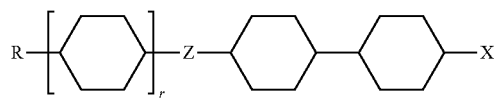

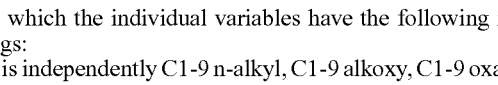

in which the individual variables have the following meanings:
R is independently C1-9 n-alkyl, C1-9 alkoxy, C1-9 oxaalkyl, C1-9 fluoroalkyl or C1-9 alkenyl;
X is selected from the group consisting of H, F, Cl, halogenated alkyl, halogenated alkenyl, halogenated alkenyloxy and halogenated alkoxy each having from 1 to 6 carbon atoms;
Z is independently —C2H4, —C4H8-, —CH=CH—, —C≡C—, —CH2O—, —COO—, —OCH2-, —OCF2-, —CF2O—, —CF=CF—, —C2F4, —C2H4CF2O— —CH2CF2- or CF2CH2-;
Y1, Y2, Y3 and Y4 are each independently of one another, H or F;
r is 0, 1 or 2; k is 0 or 1, and r+k≧2.

Other specific examples of compounds of formula II-XV are provided below:

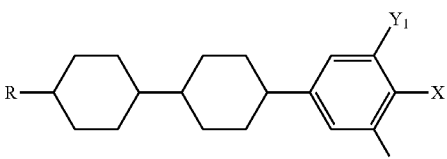

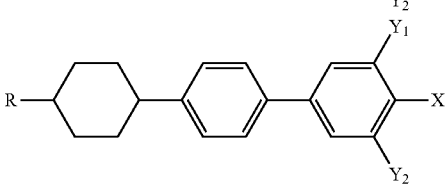

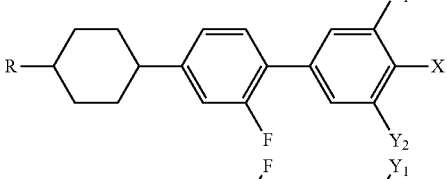

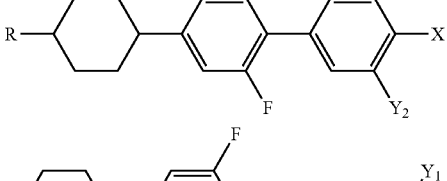

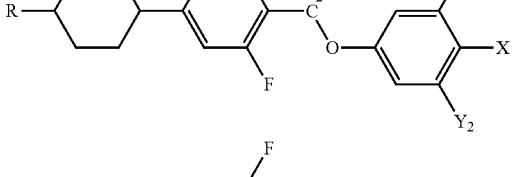

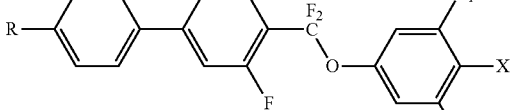

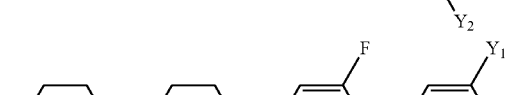

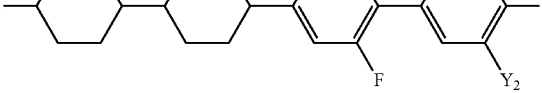

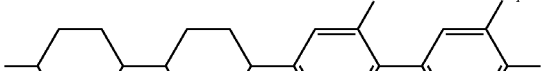

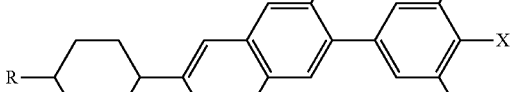

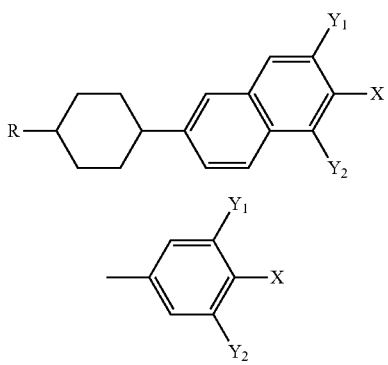

preferably has the one of the structures shown below:

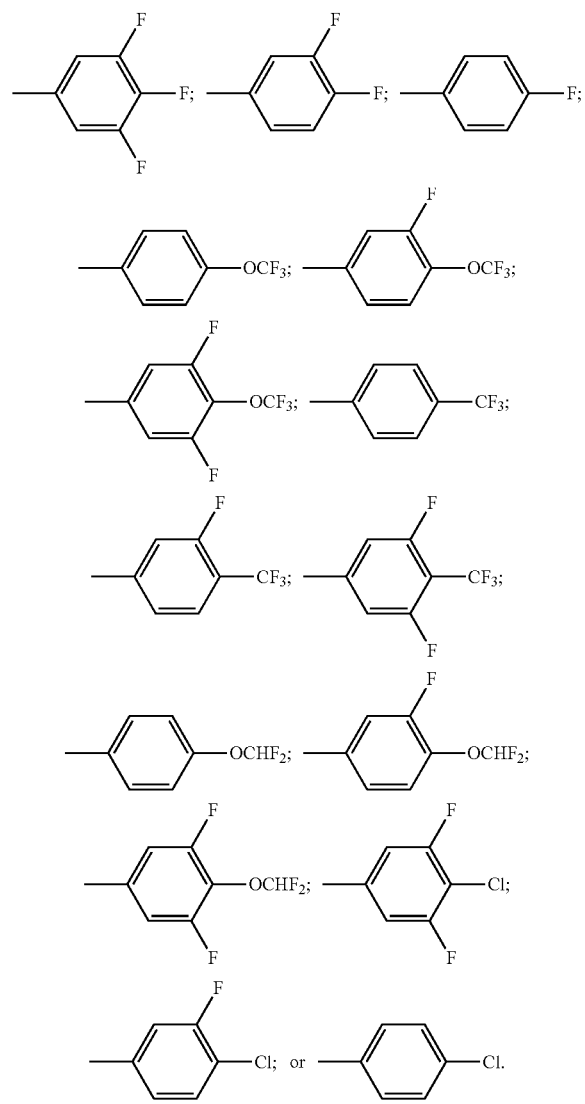

The positive dielectric constant mixture may comprise one or more compounds of the invention and one or more compounds selected from the group consisting of compounds of formulas XVI-XXIII below.

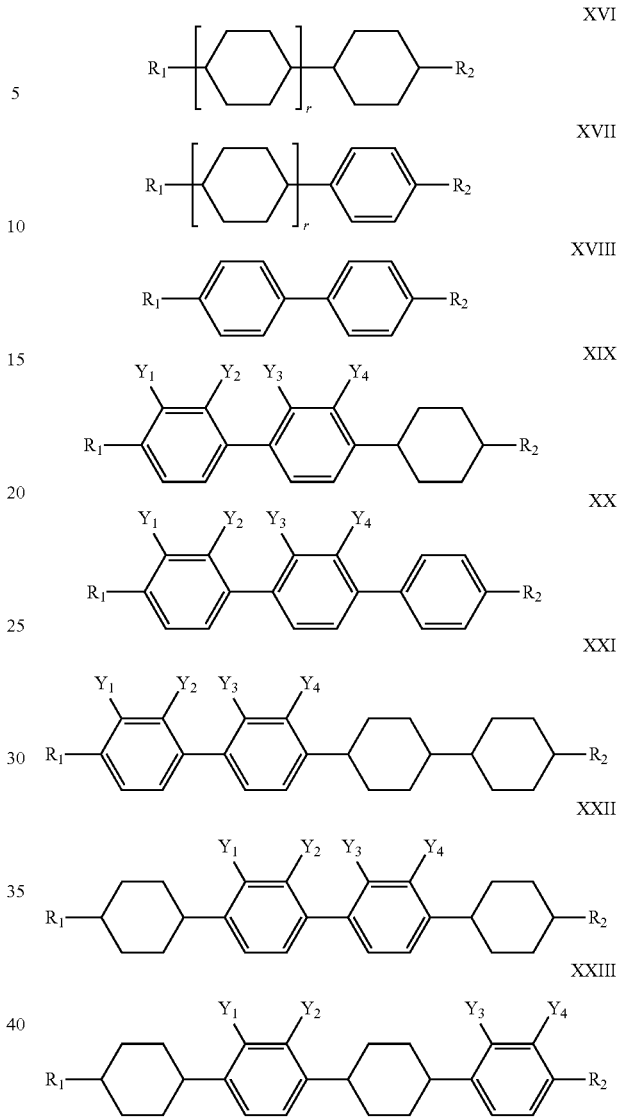

in which the individual variables have the following meanings:

R1 and R2 are each independently C1-9 n-alkyl, C1-9 alkoxy, C1-9 oxaalkyl, C1-9 alkenyl or C1-9 alkenyloxy;

Y1, Y2, Y3 and Y4 are each, independently of one another, H or F, and r is 1 or 2.

In one embodiment, the liquid crystal mixture having positive dielectric constant comprises one or more compound of Formula I-1 through I-12, one or more compounds of Formula II-XV and one or more compounds of Formula XVI-XXIII.

In one embodiment, the liquid crystal mixture has negative dielectric constant. In one embodiment, the liquid crystal mixture having negative dielectric constant comprises one or more compounds of Formula I, such as I-13 to I-25. In one embodiment, the liquid crystal mixture having negative dielectric constant comprises one or more compounds of Formula I, such as I-13 to I-25 and additionally comprises one or more compounds selected from the group consisting of compounds of the general formulae XXIV to XXXXIV shown below, where the following definitions apply:

R is C1-C8 n-alkyl, C1-C8 alkoxy, C1-C8 alkenyl or C1-C8 alkenyloxy

R' is C1-C8 alkyl, C1-C8 alkoxy, C1-C8 alkenyl or C1-C8 alkenyloxy

X1, X2, X3, X4, X5 and X6 are independently selected from the group consisting of:

H, F, Cl, CHF2 and CF3; with the proviso that at least two of X1 to X6 are independently F, Cl, CHF2 or CF3;

Z is independently selected from the group consisting of: single bond, —C2H4-, —C4H8-, —CF2O—, —OCF2-, —CF=CF—, —C2F4-, —C2H4CF2O— and —CO2-; r is 0, 1 or 2; k is 0 or 1, and r+k≧2.

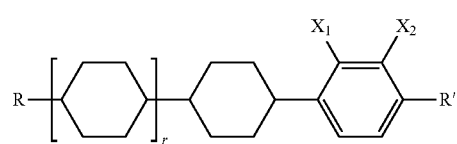
XXIV

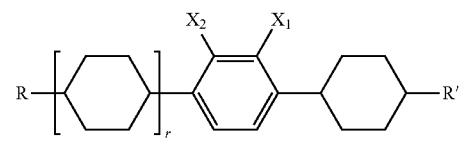
XXV

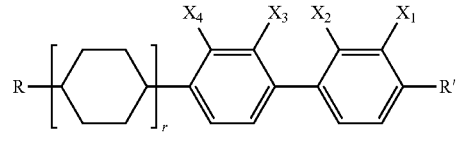
XXVI

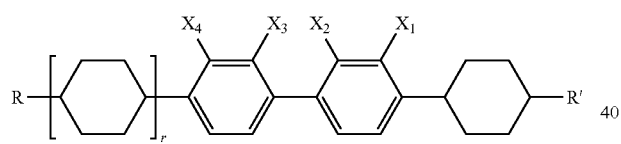
XXVII

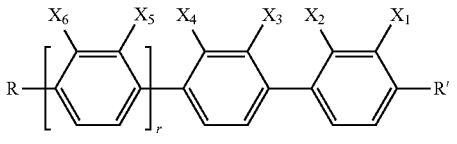
XXVIII

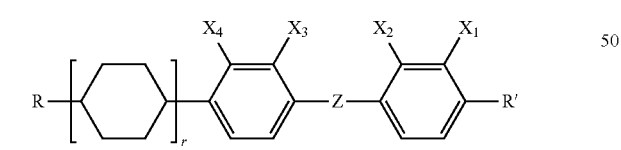
XXIX

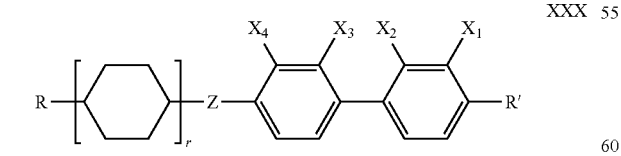
XXX

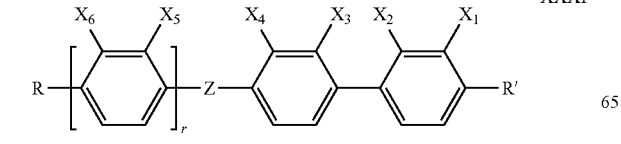
XXXI

-continued

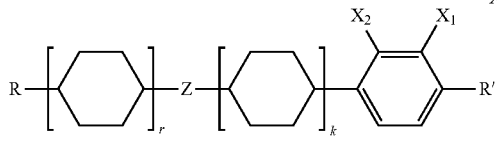
XXXII

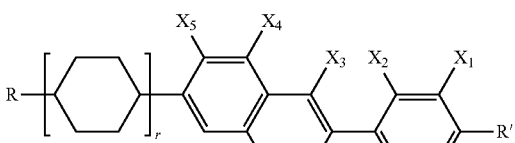
XXXIII

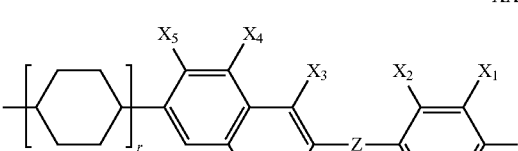
XXXIV

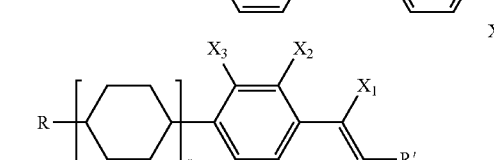
XXXV

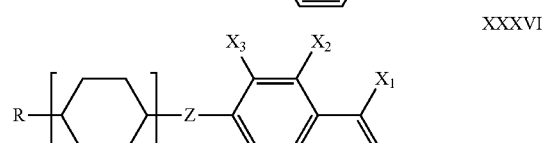
XXXVI

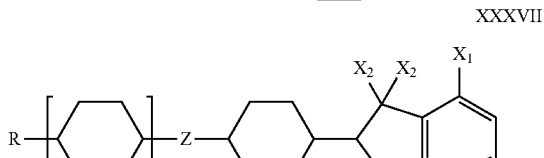
XXXVII

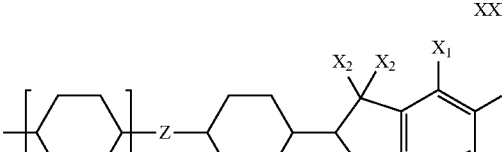
XXXVIII

XXXIX

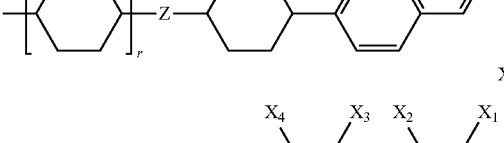
XXXX

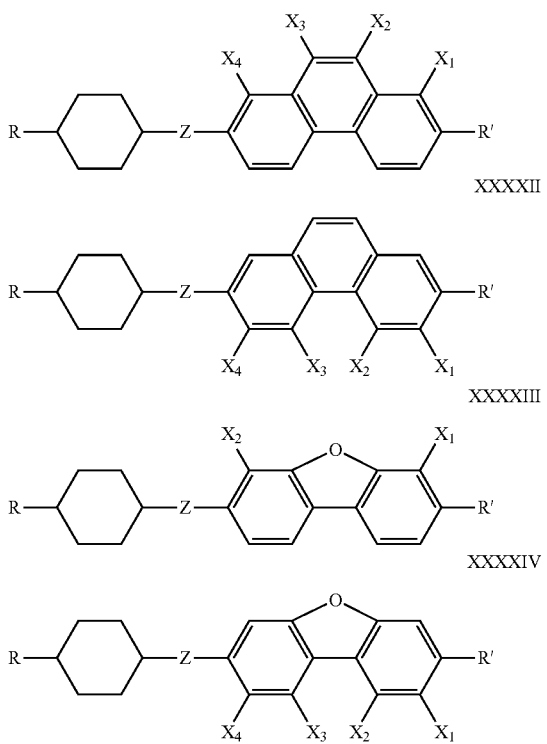

In one embodiment, the liquid crystal mixture having negative dielectric constant comprises one or more compounds of Formula I, such as I-13 to I-25 and additionally comprises one or more compounds of formulas XXXXV-XXXXVIII.

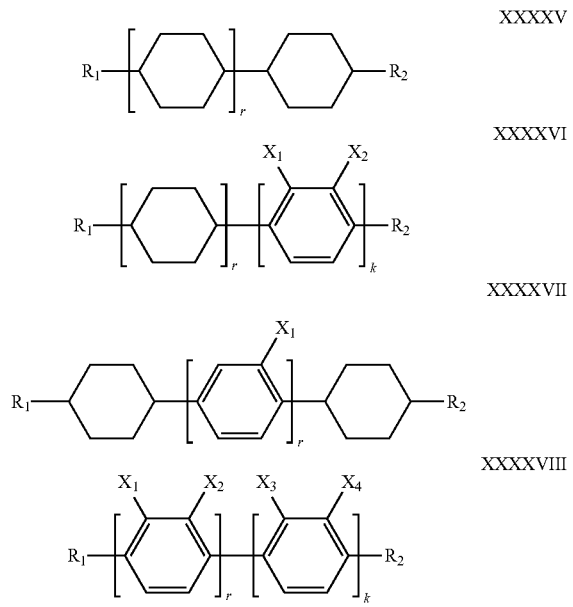

in which the individual variables have the following meanings:

R1 and R2 are each independently C1-C9 n-alkyl, C1-C9 alkoxy, C1-C9 oxaalkyl, C1-C9 alkenyl, or C1-C9 alkenyoxy;

X1, X2, X3, and X4 are each independently H or F, provided that only one of X1, X2, X3 or X4 is F;

r is 1 or 2, k is 1 or 2.

In one embodiment, the liquid crystal mixture having negative dielectric constant comprises one or more compounds of Formula I, such as I-13 to I-25, one or more compounds of formulas XXIV-XXXXIV, and one or more compounds of formulas XXXXV-XXXXVIII.

As known in the art, there are typically many components of such mixtures, as determined by the desired use of the mixture. These components can be determined by one having ordinary skill in the art without undue experimentation. The addition of one or more compounds of the invention in liquid crystal mixtures improves the properties of the mixture, including lowering threshold voltage, increasing switching speed and other properties which are known in the art. The compounds of the invention may be used in any useful amount in a liquid crystal mixture, including less than 0.1% by weight of the total composition; less than 0.5% by weight of the total composition; less than 1% by weight of the total composition, less than 3% by weight of the total composition; less than 5% by weight of the total composition; less than 7% by weight of the total composition; less than 10% by weight of the total composition; less than 20% by weight of the total composition; less than 25% by weight of the total composition; less than 30% by weight of the total composition; less than 35% by weight of the total composition; less than 40% by weight of the total composition; less than 50% by weight of the total composition; and any other useful amount.

In one embodiment, there is between 0.5% and 80% of one or more compounds of Formula I. In one embodiment, there is between 0.5% and 80% of one or more compounds of Formula I, and between 0.5% and 80% or one or more compounds of Formula II-XV. In one embodiment, there is between 0.5% and 80% of one or more compounds of Formula I, and between 0.5% and 80% of one or more compounds of Formula XVI-XXIII. In one embodiment, there is between 0.5% and 80% of one or more compounds of Formula I, between 0.5% and 80% or one or more compounds of Formula II-XV, and between 0.5% and 80% of one or more compounds of Formula XVI-XXIII. In one embodiment, there is between 0.5% and 80% of one or more compounds of Formula I, and between 0.5% and 80% or one or more compounds of Formula XXIV-XXXXIV. In one embodiment, there is between 0.5% and 80% of one or more compounds of Formula I, and between 0.5% and 80% of one or more compounds of Formula XXXXV-XXXXVIII. In one embodiment, there is between 0.5% and 80% of one or more compounds of Formula I, between 0.5% and 80% or one or more compounds of Formula XXIV-XXXXIV, and between 0.5% and 80% of one or more compounds of Formula XXXXV-XXXXVIII. There may be other components, as known in the art.

DETAILED DESCRIPTION OF THE INVENTION

The following non-limiting description provides examples of some embodiments of the invention. The synthesis of compounds of the invention not specifically exemplified here can be carried out by one of ordinary skill in the art without undue experimentation using methods known in the art.

The use of one or more compounds of the invention in mixtures having desired properties for various liquid crystal applications is known to one of ordinary skill in the art without undue experimentation.

Devices comprising one or more compounds of the invention can be made and operated by one of ordinary skill in the art without undue experimentation.

Synthesis

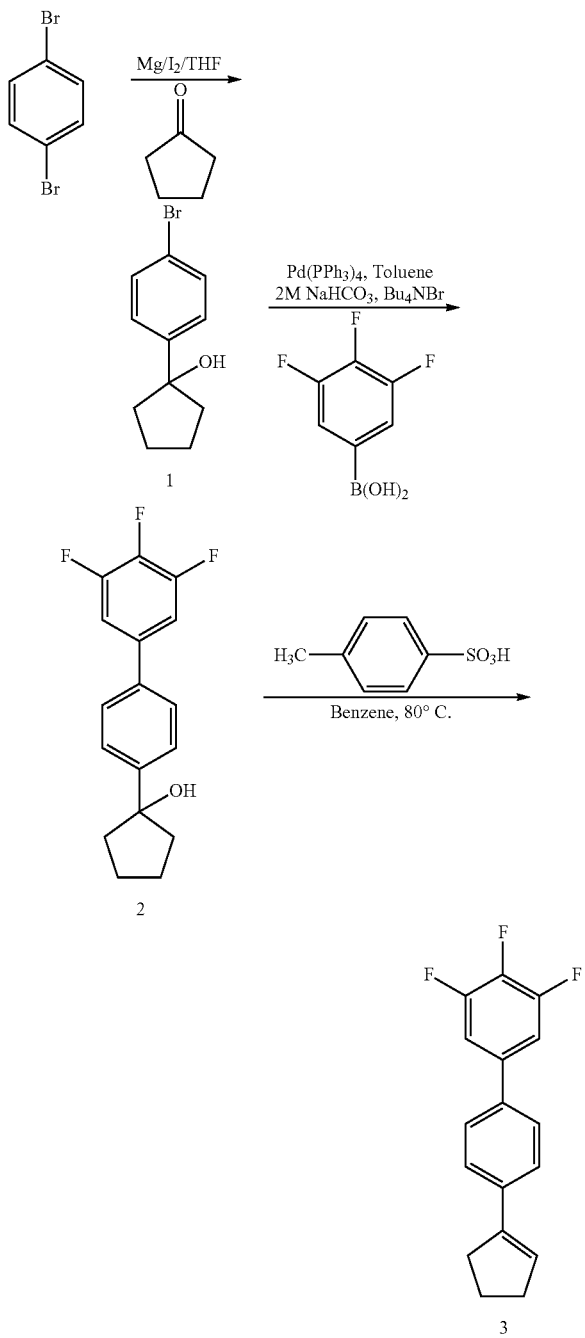

Synthesis of Compound 1:

To a flame dried round bottomed flask with a magnetic stir bar and a reflex condenser, was placed 1 gm of Mg turnings, a crystal of iodine, and about 10 mL of dry THF. With stirring, about 2 mL of a solution of 1,4-dibromobenzene (10 gm, 42 mmol) in 25 ml of dry THF was added and the reaction was initiated by a drop of 1,2-dibromoethane (if necessary). After the reaction started, the remaining THF solution was added drop wise at 50 C which maintains rapid refluxing. After the addition was complete, the resultant mixture continued to reflux for about 2 hours.

This mixture was then cooled in an ice-sodium chloride bath, and a solution of dried cyclopentanone (4.2 g, 50 mmol) in 10 ml of dry THF was added drop wise via syringe for about 20 minutes. The resultant reaction mixture was then slowly warmed to room temperature. Then refluxed for additional 4 hours and cooled to room temperature, added 50 mL of water and 50 ml of ethyl acetate. The aqueous phase was extracted with two additional 50 ml portions of ethyl acetate and all of these organic extracts were combined and dried over $MgSO_4$. The crude product obtained was passed through a column of silica gel using 10% EA in hexane as eluent. Yield of the product: 6.5 g (64%).

Synthesis of Compound 2:

A flame dried 500 ml round-bottomed flask with a magnetic stir bar, was charged with compound 1 (2.5 g, 10 mmol), 3,4,5-trifluorophenyl boronic acid (2.35 g, 11.4 mmol), 50 ml toluene, 2M $NaHCO_3$ (50 ml), $Bu_4NBr$ (25 mg) and the mixture flushed with argon for 15 min. $[Pd(PPh_3)_4]$ (0.25 g) was added and the mixture heated under argon at ~85° C. for 12 h, with good stirring. After cooling to room temperature, 50 ml water was added, extracted with 3×25 ml ethyl acetate, organic extract dried ($MgSO_4$), filtered over a bed of celite and solvent removed from filtrate under reduced pressure. The crude product was then passed through a column of silica gel using 10% EA in hexane as eluent. Yield, 3.0 g; 90%).

Synthesis of Compound 3:

A magnetic stir bar, 2 g of compound 2, 50 ml of benzene, and 0.2 g of p-toluene-sulfonic acid were placed in a 50 ml of round bottomed flask connected with a Dean-stark apparatus. The resulting solution was then refluxed at 80 C overnight, cooled to room temperature and extracted using ethyl acetate. The crude product was then passed through a column of silica gel using hexane as eluent. The product was further crystallized from a mixture of chloroform and acetonitrile. Yield: 1.5 g (80%).

Incorporation of Deuterium into Structures:

Methods of incorporating one or more deuterium atoms into a structure are known in the art.

Characterization methods and property analysis of compounds and mixtures are well-known in the art. Methods to alter the material properties of a mixture, such as adding other compound to a mixture, or by adding more or less of a compound in a mixture, are also known in the art.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds provided in the prior art with an enabling disclosure, including certain compounds disclosed in the references disclosed herein (particularly in referenced patent documents), are not intended to be included in the claim and are intended to be able to be removed individually or collectively.

When a group of substituents is disclosed herein, it is understood that all individual members of those groups and all subgroups, including any isomers and enantiomers of the group members, and classes of compounds that can be formed using the substituents are disclosed separately. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, device elements, starting materials, synthetic methods, and mixture constituents other than those specifically exemplified can be employed in the practice of the invention without resort to undue experimentation. All art-known functional equivalents, of any such methods, device elements, starting materials, synthetic methods, and mixture constituents are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. The definitions are provided to clarify their specific use in the context of the invention.

One skilled in the art would readily appreciate that the present invention is well adapted to carry out the objects and obtain the ends and advantages mentioned, as well as those inherent therein. The liquid crystal compounds and methods described herein as presently representative of preferred embodiments are exemplary and are not intended as limitations on the scope of the invention. Changes therein and other uses will occur to those skilled in the art, which are encompassed within the spirit of the invention, are defined by the scope of the claims.

Although the description herein contains many specificities, these should not be construed as limiting the scope of the invention, but as merely providing illustrations of some of the embodiments of the invention. Thus, additional embodiments are within the scope of the invention and within the claims. All references cited herein are hereby incorporated by reference to the extent that there is no inconsistency with the disclosure of this specification. Some references provided herein are incorporated by reference herein to provide details concerning additional starting materials, additional methods of synthesis, additional methods of analysis and additional uses of the invention.

We claim:
1. A compound having the formula:

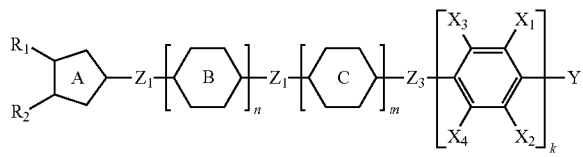

where

wherein one or more hydrogen atoms on the A ring may be replaced with one or more halogen atoms;

$R^1$ and $R^2$, independently of one another, are selected from the group consisting of: H and unsubstituted or monosubstituted alkyl having 1-12 carbon atoms, wherein substitution is halogen or CN, wherein one or more $CH_2$ groups of the alkyl group may be independently replaced by —O—, —S—, —CO—, —CO—O—, —O—CO—, —O—CO—O— or —CH═CH—, provided that heteroatoms are not directly connected;

B and C are each independently selected from the group consisting of: 1,4-cyclohexene, cyclohexenyl, 1,4-phenyl, 1,3-dioxan-5,2-diyl, Pyridin-5,2-diyl, pyrimidin-5,2-diyl, naphthalene-2,6-diyl, trans-decahydronaphthalene-2,6-diyl, tetrahydronaphthalene-2,6-diyl, indeneyl, phenanthryl, and dibenzo[b,d]furan; in which one or more hydrogen atoms in any ring structure may be independently replaced by one or more halogen atoms;

Z1 is a single bond or —(CH$_2$)$_k$—, where k is an integer from 1 to 8; and wherein one or more hydrogen atoms may be replaced by halogen or CN, and one or more $CH_2$ groups may be independently replaced by —O—, —S—, —CO—, —CO—O—, —O—CO—, —O—CO—O—, —CH=CH—, or —C≡C—, provided that heteroatoms are not directly connected;

Z2, and Z3 are each independently selected from the group consisting of: a single bond, —(CH$_2$)$_2$—, —(CH$_2$)$_4$—, —CH=CHCH$_2$CH$_2$—, —CH$_2$CH$_2$CH=CH—, CF$_2$O, OCF$_2$, CF$_2$CF$_2$, CF=CF, CH$_2$CF$_2$, CF$_2$CH$_2$, OCF2CF2O, C2H4CF2O, CH$_2$O, OCH$_2$, —CH=CH—, —C≡C—, and COO;

K=0,1;

n and m are independently 0, 1, or 2; wherein K+n+m≧2;

X1, X2, X3 and X4 are independently in each instance selected from the group consisting of: H, F, Cl, CF$_3$, CHF$_2$, and CN;

Y is selected from the group consisting of: H, F, Cl, CN, NCS, OCHF$_2$, CHF$_2$, OCF$_3$, CF$_3$, C$_{1-20}$ alkyl, C$_{1-20}$ alkoxy, C$_{1-20}$ alkenyl, and C$_{1-20}$alkenyloxy wherein one or more hydrogen atoms in the alkyl, alkoxy, alkenyl, alkenyloxy groups may be independently substituted by one or more halogen atoms;

and where one or more hydrogen atoms may be replaced with deuterium;

provided that the linker between the A ring and the next ring is not —OC(=O)—; —OCH$_2$—; or —CH$_2$CH$_2$— and provided that when A is

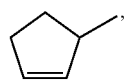

the linker between the A ring and the next ring is not —C$_n$H$_{2n}$O—, where n is 5 to 20; and provided that when A is

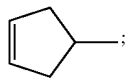

Y is selected from F, Cl, CN, NCS.

2. The compound of claim 1 having a positive dielectric constant.

3. A compound of claim 2, having formula

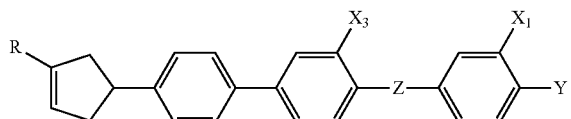

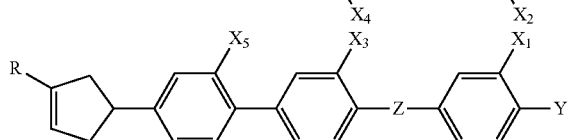

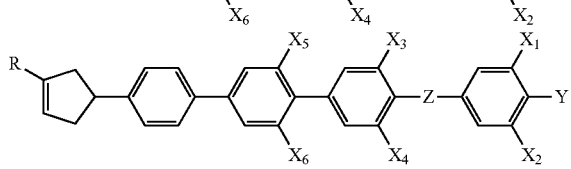

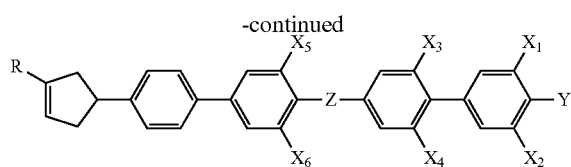

or formula I-1 through I-12

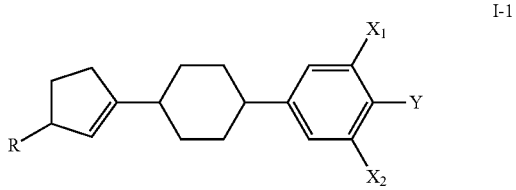

I-1

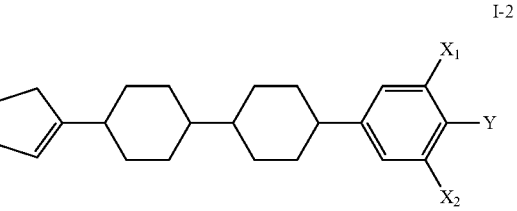

I-2

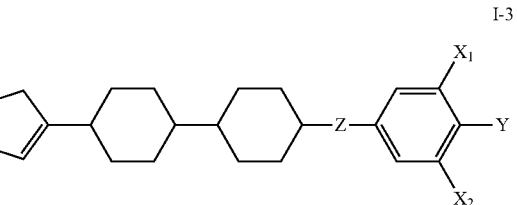

I-3

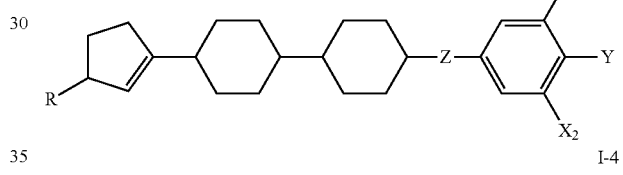

I-4

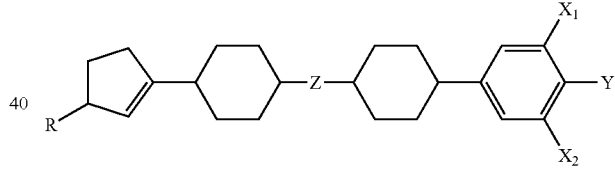

I-5

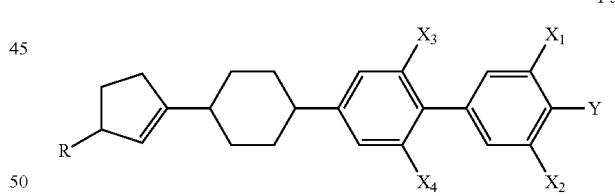

I-6

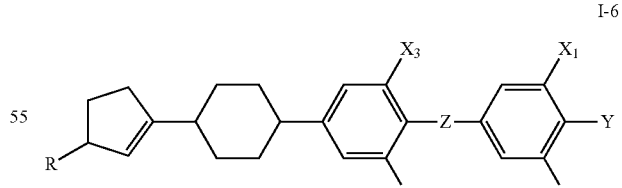

I-7

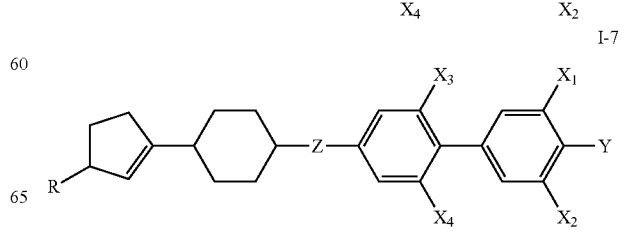

-continued
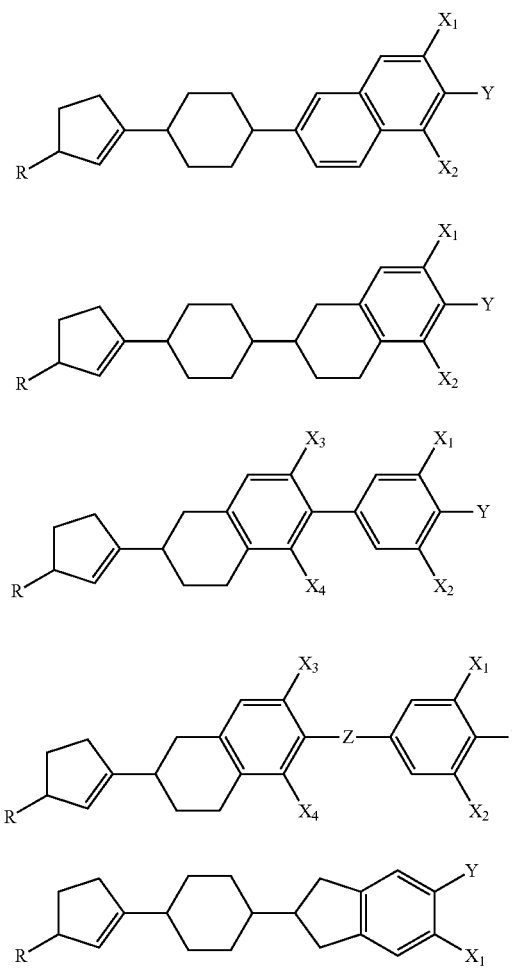
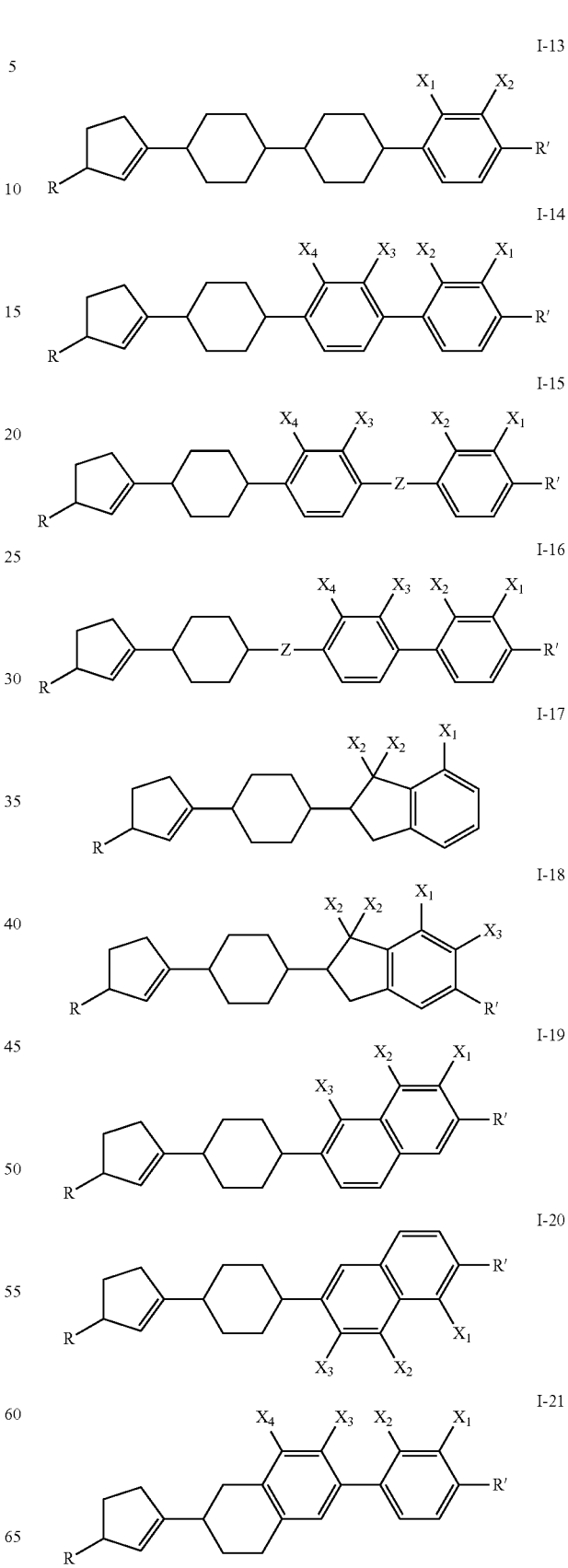
where R is C1-C7 n-alkyl;
Y is independently selected from the group consisting of: F, Cl, CF3, OCF3, OCHF2, and OCF2CF3;
X1, X2, X3, X4, X5 and X6 are each, independently of one another, H or F;
Z is independently —C2H4-, —CF2O—, —CF═CF—, —C2F4-, or —CO2-.
4. The compound of claim 1 having a negative dielectric constant.
5. The compound of claim 4, having formula
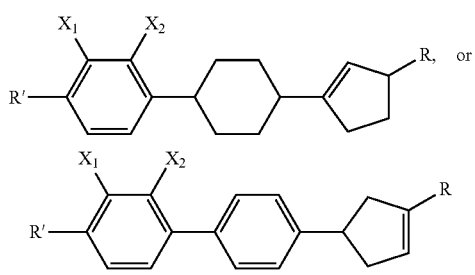
or formula I-13 through I-25

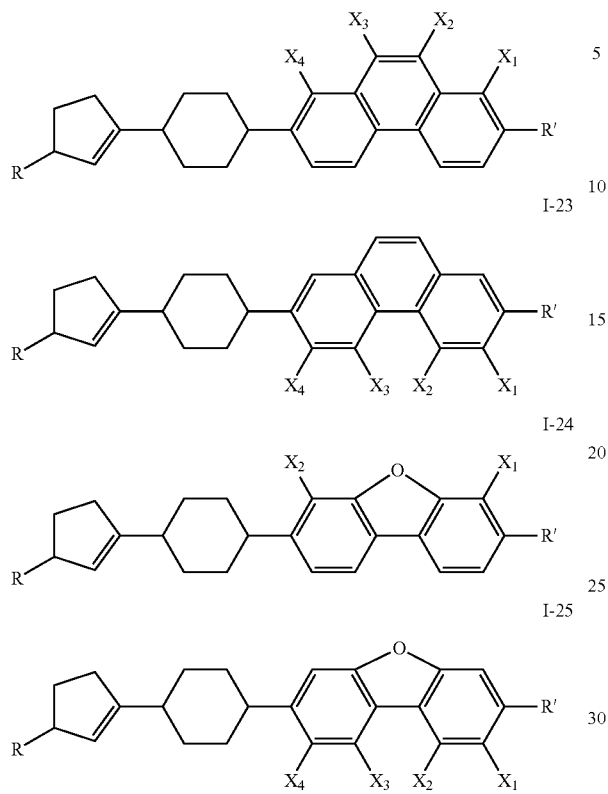

where R is C1-C7 n-alkyl;

R' is C1-C7 alkyl, alkenyl, alkoxy, or alkenyloxy;

X1, X2, X3 and X4 are independently selected from the group consisting of: H, F, Cl, CHF2 and CF3; with the proviso that at least two of X1 to X4 are independently F, Cl, CHF2 or CF3;

Z is independently selected from the group consisting of: —C2H4-, —CF2O—, —CF=CF—, —C2F4-, and —CO2-.

6. A liquid crystal mixture having positive dielectric constant comprising a compound of claim 1.

7. The mixture of claim 6, wherein the mixture further comprises at least one compound of formula II-XV

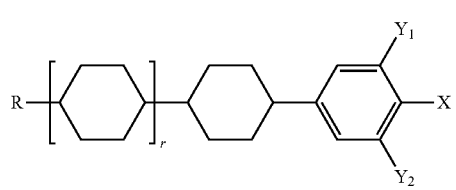

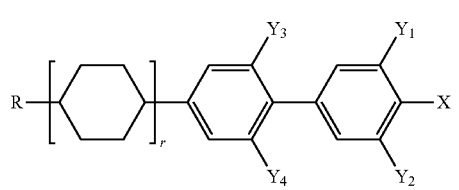

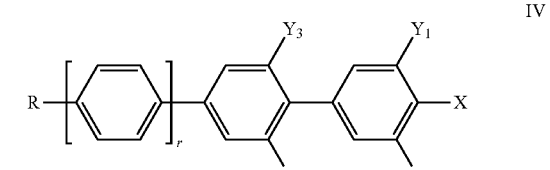

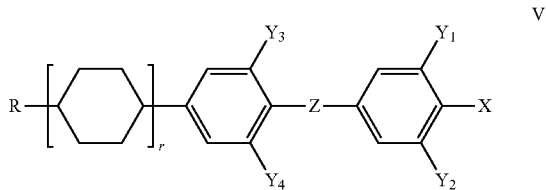

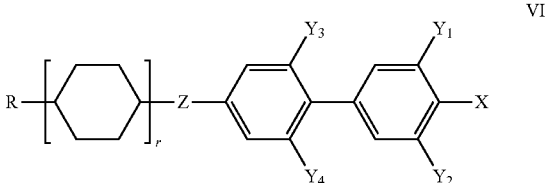

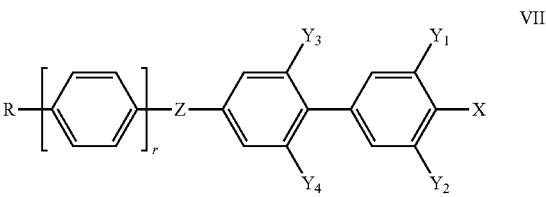

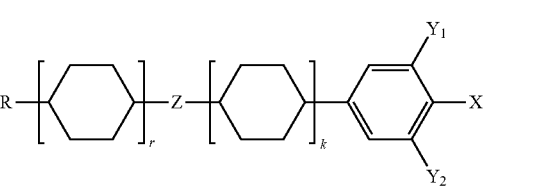

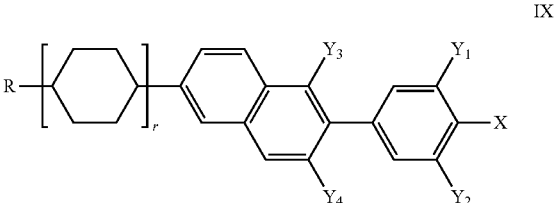

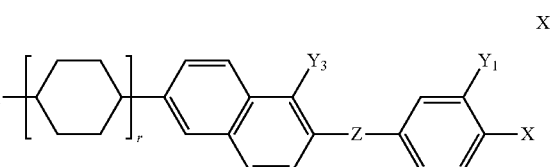

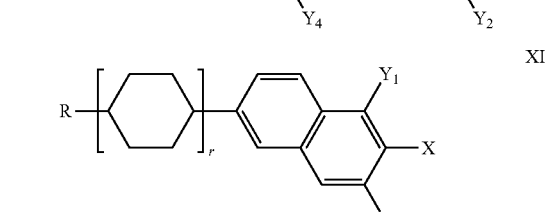

-continued

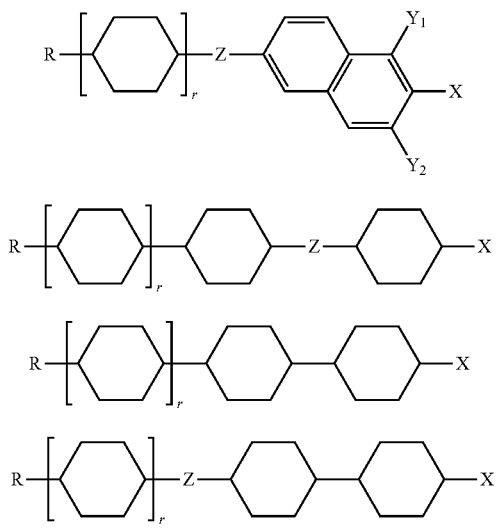

XII

XIII

XIV

XV where

R is independently C1-9 n-alkyl, C1-9 alkoxy, C1-9 oxaalkyl, C1-9 fluoroalkyl or C1-9 alkenyl;

X is selected from the group consisting of H, F, Cl, halogenated alkyl, halogenated alkenyl, halogenated alkenyloxy and halogenated alkoxy each having from 1 to 6 carbon atoms;

Z is independently —C2H4, —C4H8-, —CH═CH—, —C≡C—, —CH2O—, —COO—, —OCH2-, —OCF2-, —CF2O—, —CF═CF—, —C2F4, —C2H4CF2O— —CH2CF2- or CF2CH2-;

Y1, Y2, Y3 and Y4 are each independently of one another, H or F;

r is 0, 1 or 2; k is 0 or 1, and r+k≧2.

8. The mixture of claim 6, wherein the mixture further comprises at least one compound of formula XVI-XXIII

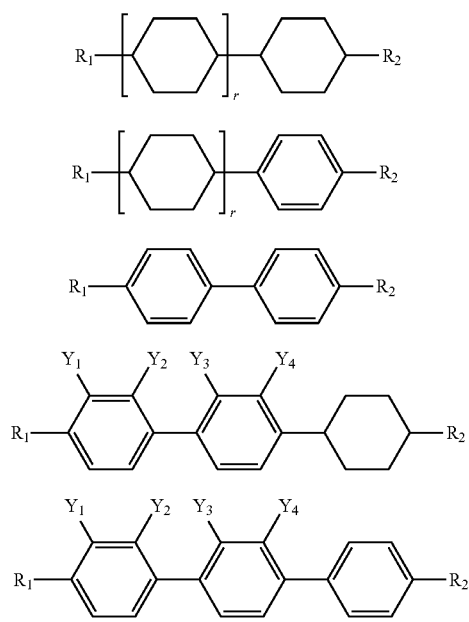

XVI

XVII

XVIII

XIX

XX

-continued

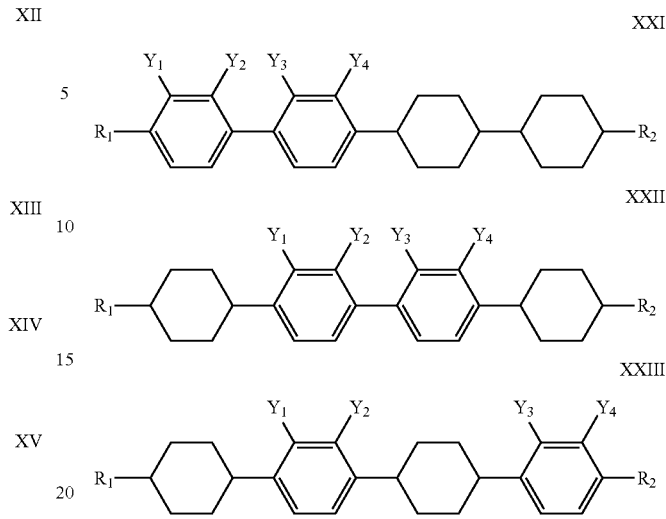

XXI

XXII

XXIII where

R1 and R2 are each independently C1-9 n-alkyl, C1-9 alkoxy, C1-9 oxaalkyl, C1-9 alkenyl or C1-9 alkenyloxy;

Y1, Y2, Y3 and Y4 are each, independently of one another, H or F, and r is 1 or 2.

9. The mixture of claim 6, wherein the mixture further comprises at least one compound of formula II-XV

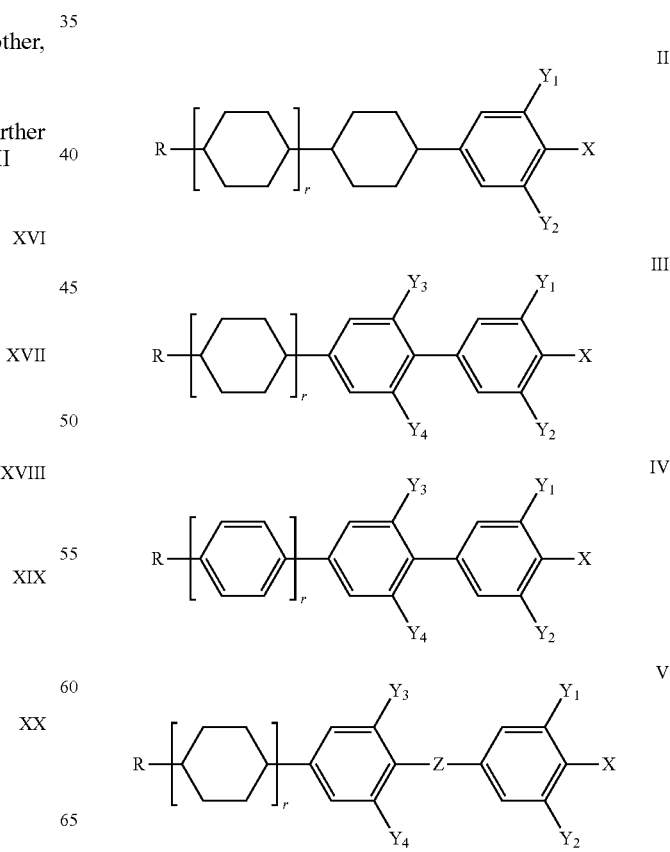

II

III

IV

V

-continued

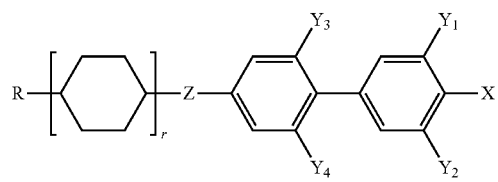
VI

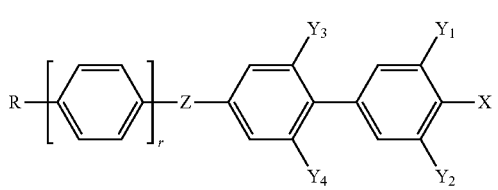
VII

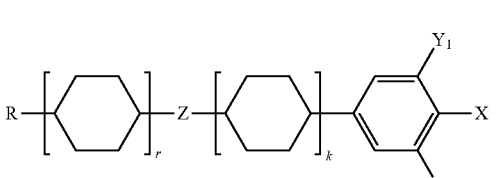
VIII

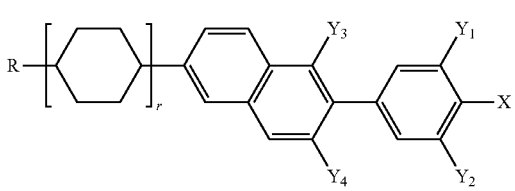
IX

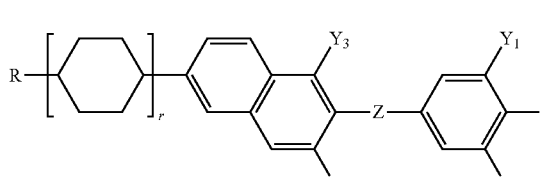
X

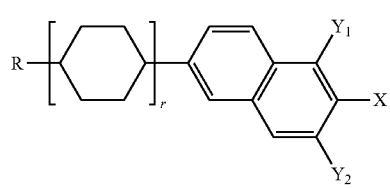
XI

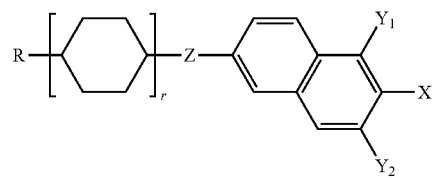
XII

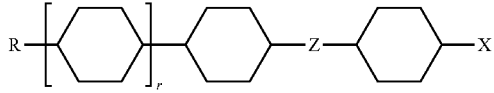
XIII

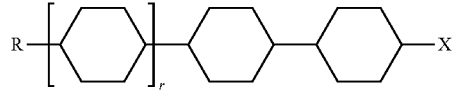
XIV

-continued

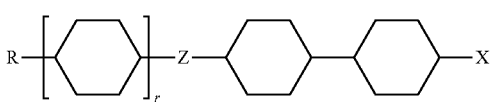
XV where

R is independently C1-9 n-alkyl, C1-9 alkoxy, C1-9 oxaalkyl, C1-9 fluoroalkyl or C1-9 alkenyl;

X is selected from the group consisting of H, F, Cl, halogenated alkyl, halogenated alkenyl, halogenated alkenyloxy and halogenated alkoxy each having from 1 to 6 carbon atoms;

Z is independently —C2H4, —C4H8-, —CH═CH—, —C≡C—, —CH2O—, —COO—, —OCH2-, —OCF2-, —CF2O—, —CF═CF—, —C2F4, —C2H4CF2O— —CH2CF2- or CF2CH2-;

Y1, Y2, Y3 and Y4 are each independently of one another, H or F;

r is 0, 1 or 2; k is 0 or 1, and r+k≧2 and at least one compound of formula XVI-XXIII

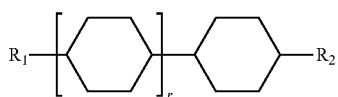
XVI

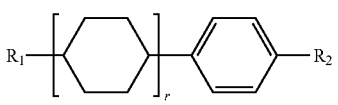
XVII

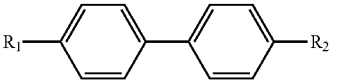
XVIII

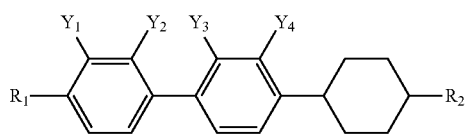
XIX

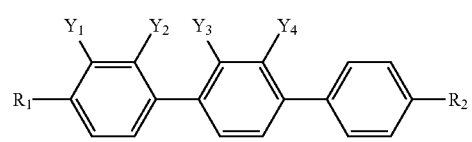
XX

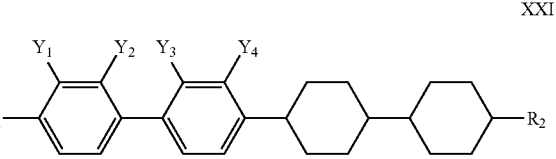
XXI

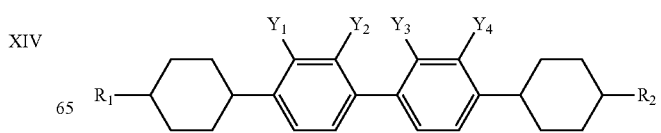
XXII

-continued

XXIII

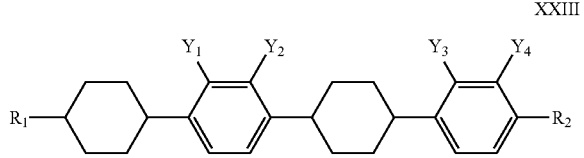

where

R1 and R2 are each independently C1-9 n-alkyl, C1-9 alkoxy, C1-9 oxaalkyl, C1-9 alkenyl or C1-9 alkenyloxy;

Y1, Y2, Y3 and Y4 are each, independently of one another, H or F, and r is 1 or 2.

10. A liquid crystal mixture having negative dielectric constant comprising a compound of claim 1.

11. The mixture of claim 10, wherein the mixture further comprises at least one compound of formula XXIV-XXXXIV XXIV
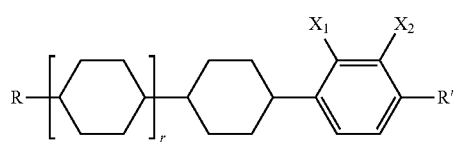

XXV
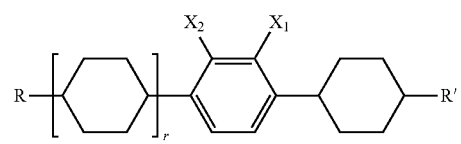

XXVI
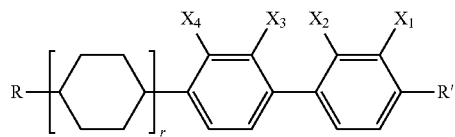

XXVII
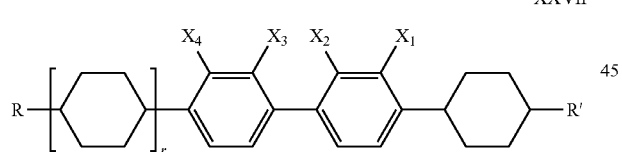

XXVIII
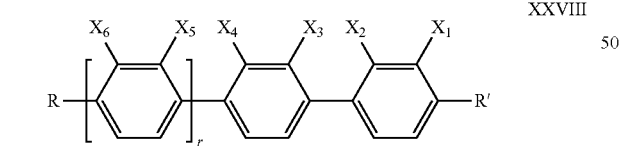

XXIX
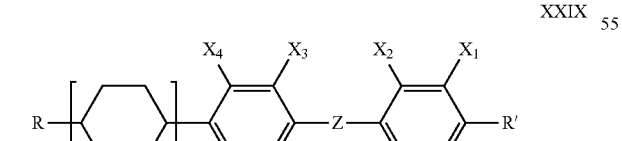

XXX
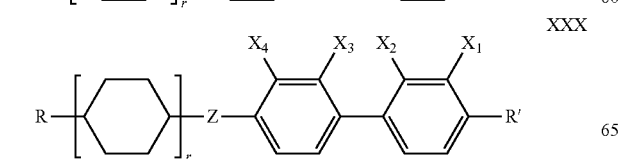

XXXI
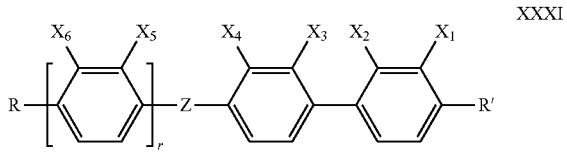

XXXII
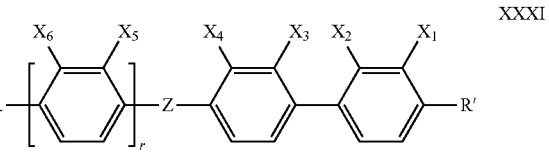

XXXIII
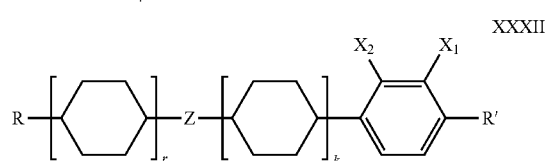

XXXIV
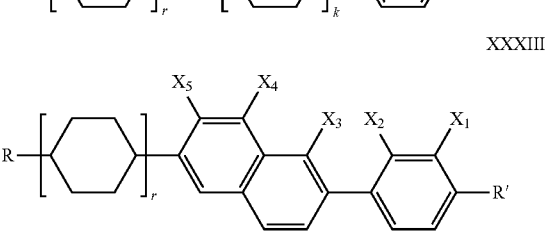

XXXV
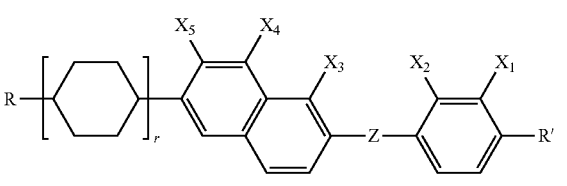

XXXVI
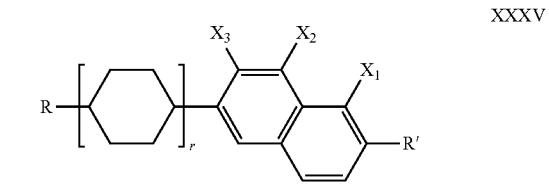

XXXVII
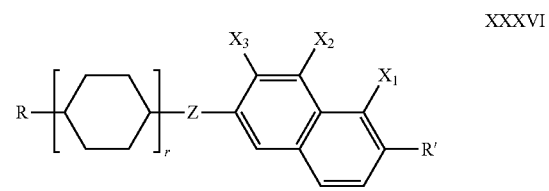

XXXVIII
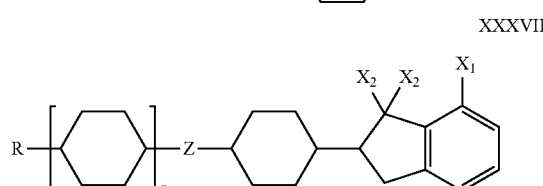

XXXIX
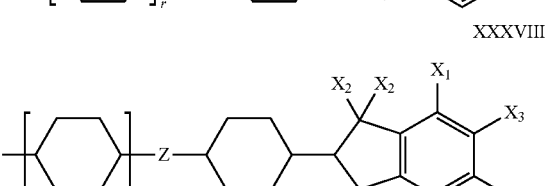

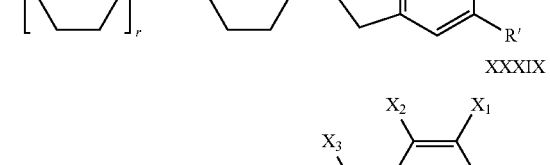

XXXX
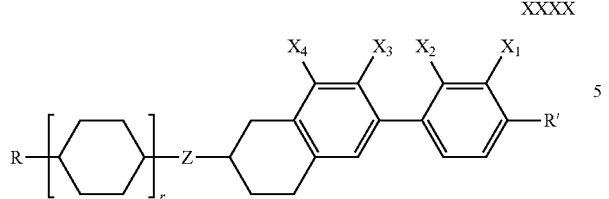

XXXXI
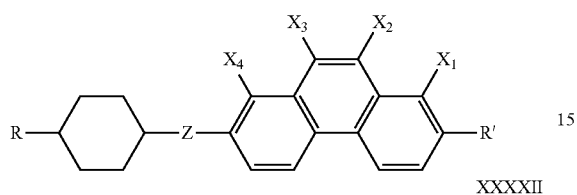

XXXXII
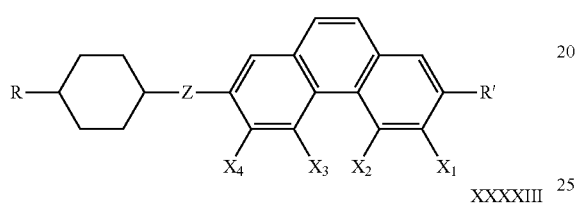

XXXXIII
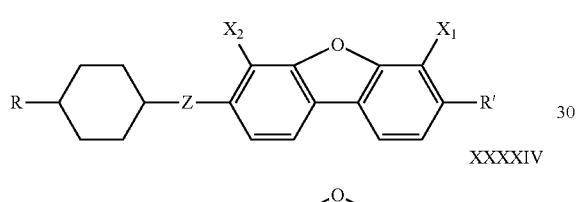

XXXXIV
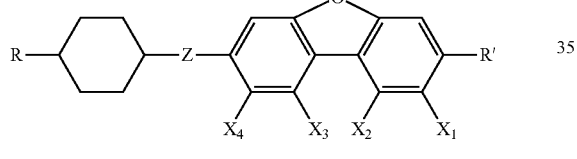

where R is C1-C8 n-alkyl, C1-C8 alkoxy, C1-C8 alkenyl or C1-C8 alkenyloxy

R' is C1-C8 alkyl, C1-C8 alkoxy, C1-C8 alkenyl or C1-C8 alkenyloxy X1, X2, X3, X4, X5 and X6 are independently selected from the group consisting of: H, F, Cl, CHF2 and CF3; with the proviso that at least two of X1 to X6 are independently F, Cl, CHF2 or CF3;

Z is independently selected from the group consisting of: single bond, —C2H4-, —C4H8-, —CF2O—, —OCF2-, —CF=CF—, —C2F4-, —C2H4CF2O— and —CO2-; r is 0, 1 or 2; k is 0 or 1, and r+k≧2.

12. The mixture of claim 10, wherein the mixture further comprises at least one compound of formula XXXXV-XXXXVIII XXXXV

XXXXVI
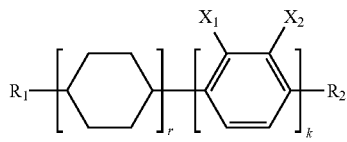

XXXXVII
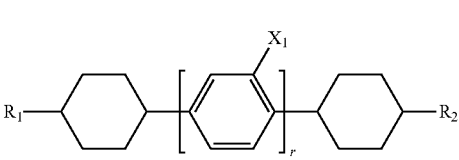

XXXXVIII
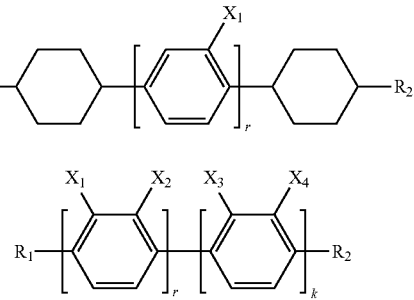

where

R1 and R2 are each independently C1-C9 n-alkyl, C1-C9 alkoxy, C1-C9 oxaalkyl, C1-C9 alkenyl, or C1-C9 alkenyoxy;

X1, X2, X3, and X4 are each independently H or F, provided that only one of X1, X2, X3 or X4 is F;

r is 1 or 2, k is 1 or 2.

13. The mixture of claim 10, wherein the mixture further comprises at least one compound of formula XXIV-XXXXIV XXIV
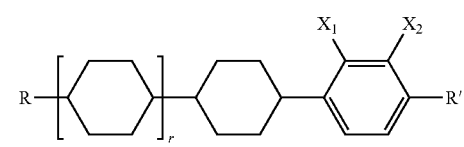

XXV
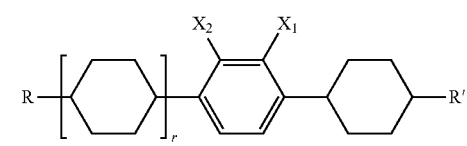

XXVI
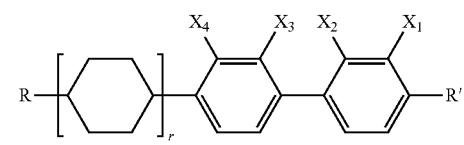

XXVII
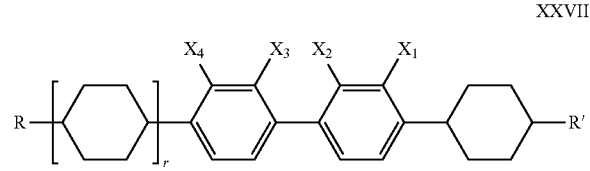

XXVIII
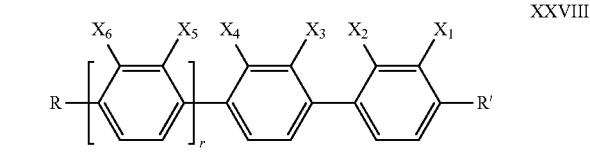

XXIX
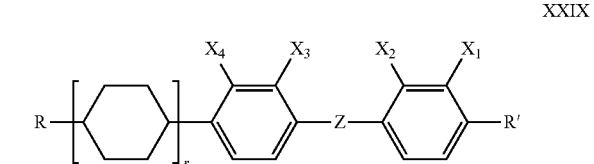

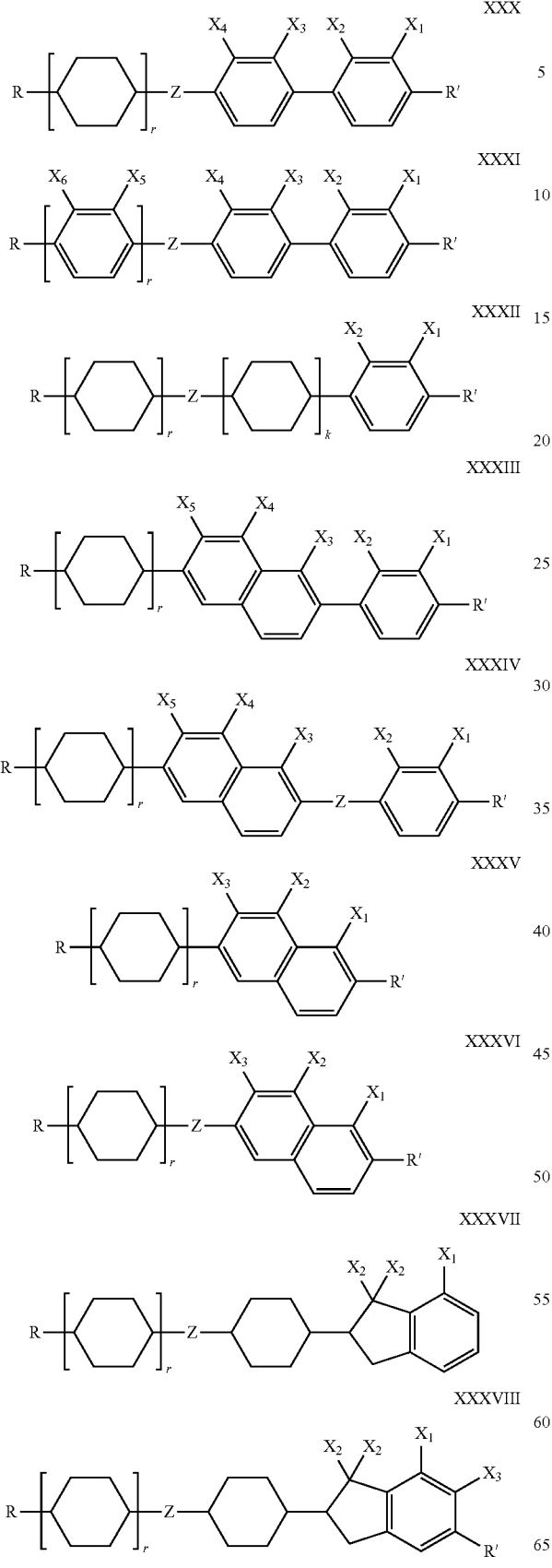
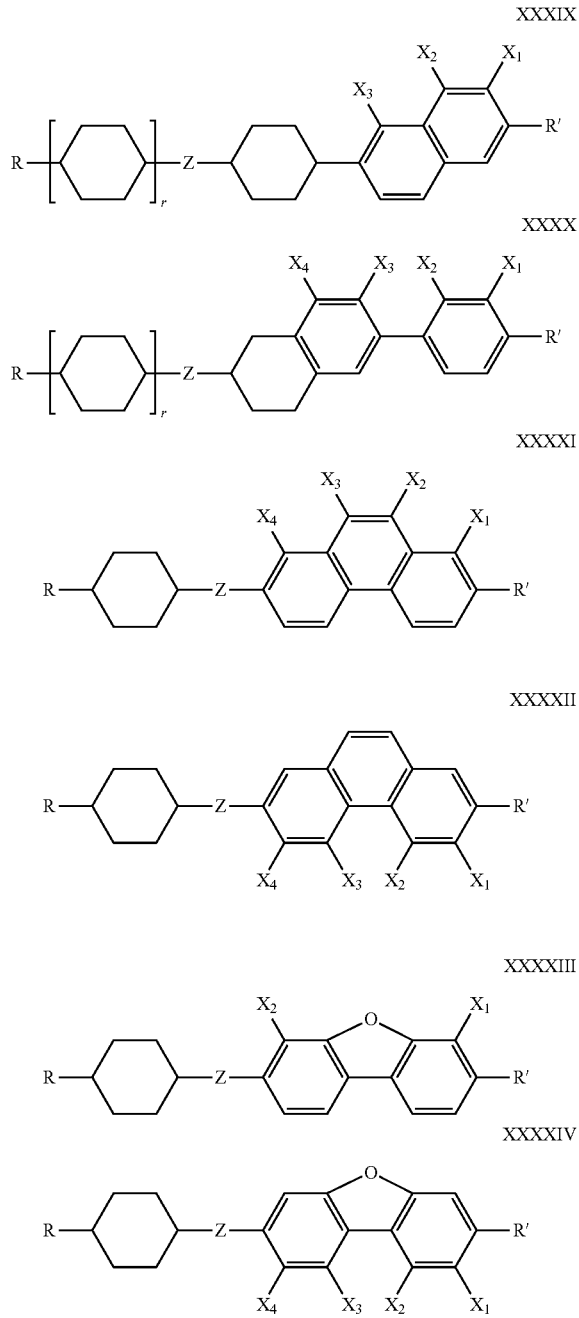

where R is C1-C8 n-alkyl, C1-C8 alkoxy, C1-C8 alkenyl or C1-C8 alkenyloxy

R' is C1-C8 alkyl, C1-C8 alkoxy, C1-C8 alkenyl or C1-C8 alkenyloxy

X1, X2, X3, X4, X5 and X6 are independently selected from the group consisting of: H, F, Cl, CHF2 and CF3; with the proviso that at least two of X1 to X6 are independently F, Cl, CHF2 or CF3;

Z is independently selected from the group consisting of: single bond, —C2H4-, —C4H8-, —CF2O—, —OCF2-, —CF═CF—, —C2F4-, —C2H4CF2O— and —CO2-; r is 0, 1 or 2; k is 0 or 1, and r+k≧2 and at least one compound of formula XXXXV-XXXXVIII

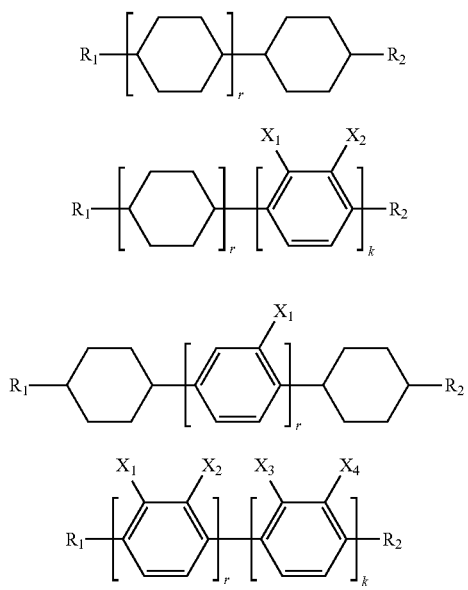

XXXXV
XXXXVI
XXXXVII
XXXXVIII where

R1 and R2 are each independently C1-C9 n-alkyl, C1-C9 alkoxy, C1-C9 oxaalkyl, C1-C9 alkenyl, or C1-C9 alkenyoxy;

X1, X2, X3, and X4 are each independently H or F, provided that only one of X1, X2, X3 or X4 is F;

r is 1 or 2, k is 1 or 2.

14. A device comprising a compound of claim 1.

15. A device comprising a mixture of claim 4.

16. The compound of claim 1, wherein one or more hydrogen atoms in any ring is substituted with deuterium.

17. The compound of claim 1, wherein one or more hydrogen atoms in any non-ring structure is substituted with deuterium.

18. The compound having formula:

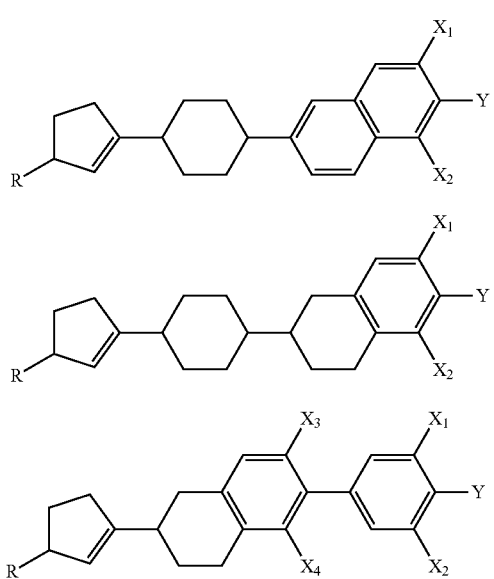

I-8
I-9
I-10

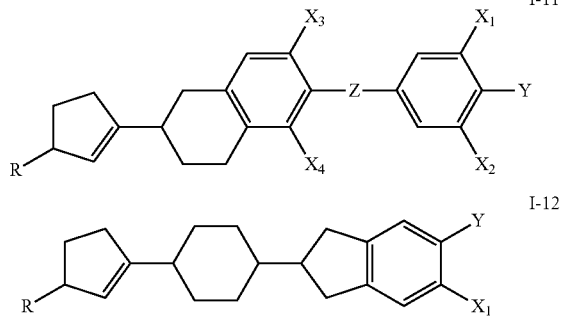

I-11
I-12

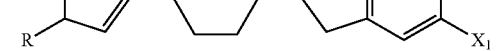

where in formula I-8 to I-12, R is C1-C7 n-alkyl;

Y is independently selected from the group consisting of: F, Cl, CF3, OCF3, OCHF2, and OCF2CF3;

X1, X2, X3, X4, X5 and X6 are each, independently of one another, H or F;

Z is independently —C2H4-, —CF2O—, —CF=CF—, —C2F4-, or —CO2-;

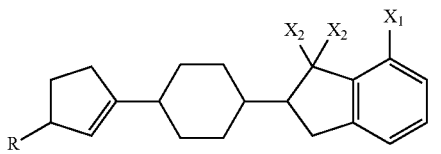

I-17

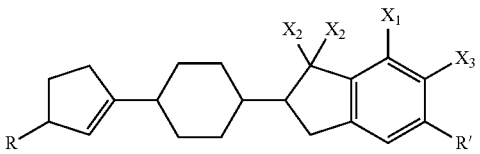

I-18

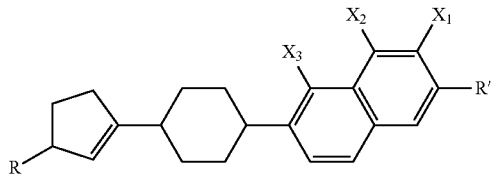

I-19

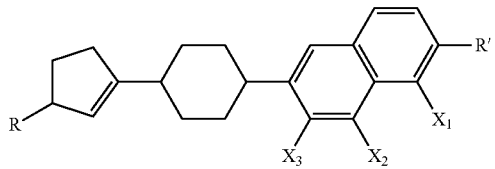

I-20

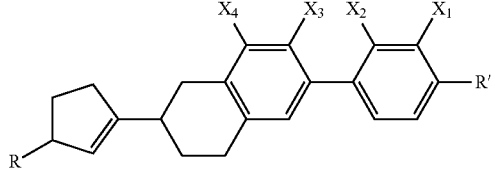

I-21

-continued

I-22
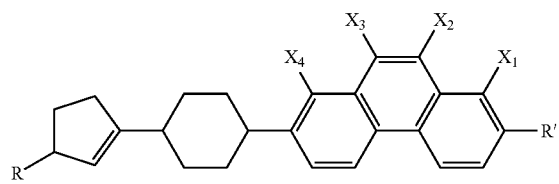

I-23
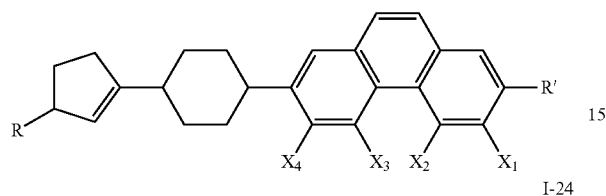

I-24
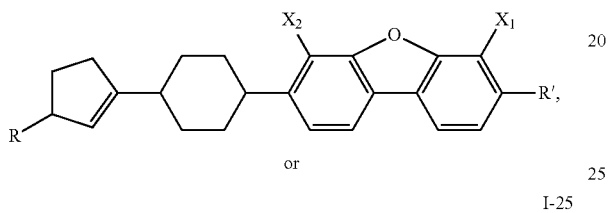

I-25
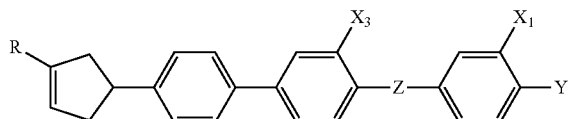

where for formula I-17 to I-25, R is C1-C7 n-alkyl;

R' is C1-C7 alkyl, alkenyl, alkoxy, or alkenyloxy;

X1, X2, X3 and X4 are independently selected from the group consisting of: H, F, Cl, CHF2 and CF3; with the proviso that at least two of X1 to X4 are independently F, Cl, CHF2 or CF3;

Z is independently selected from the group consisting of: —C2H4-, —CF2O—, —CF=CF—, —C2F4-, and —CO2—.

19. The compound having formula:

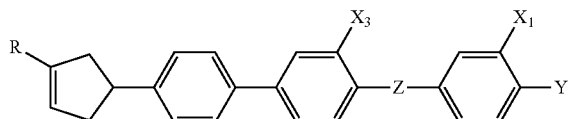

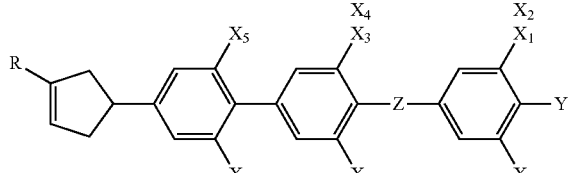

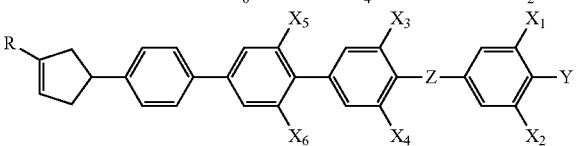

-continued

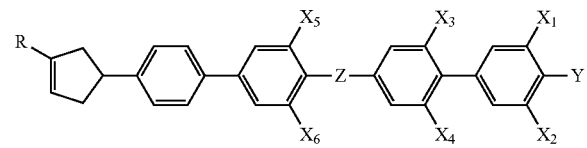

I-1
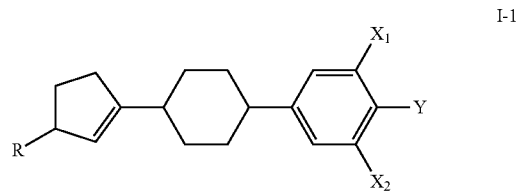

I-2
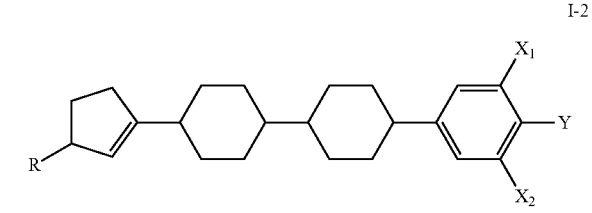

I-3
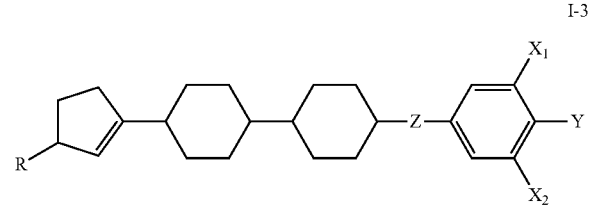

I-4
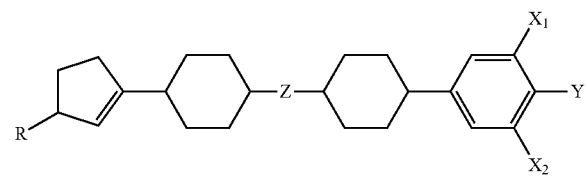

I-5
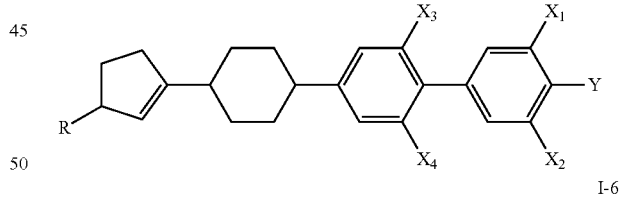

I-6
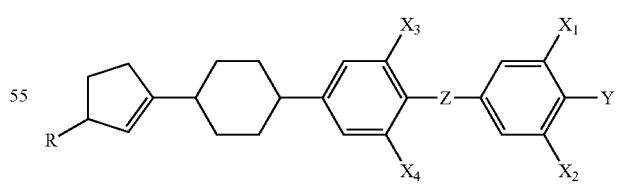

I-7
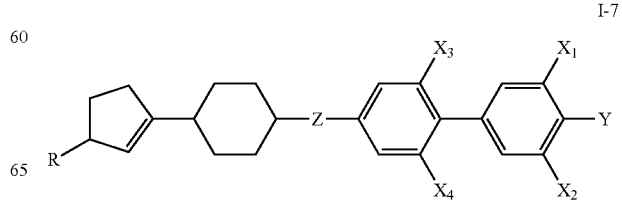

-continued
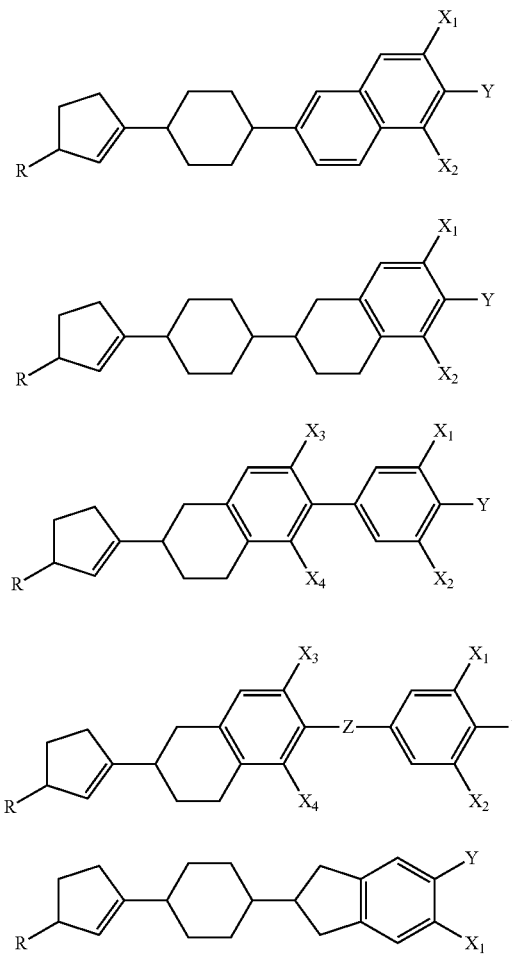
where R is C1-C7 n-alkyl;
Y is independently selected from the group consisting of: F, Cl, CF3, OCF3, OCHF2, and OCF2CF3;
X1, X2, X3, X4, X5 and X6 are each, independently of one another, H or F;
Z is independently —C2H4—, —CF2O—, —CF=CF—, —C2F4-, or —CO2-;
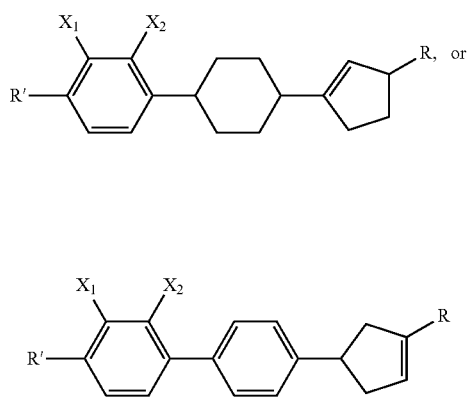
or formula I-13 through I-25
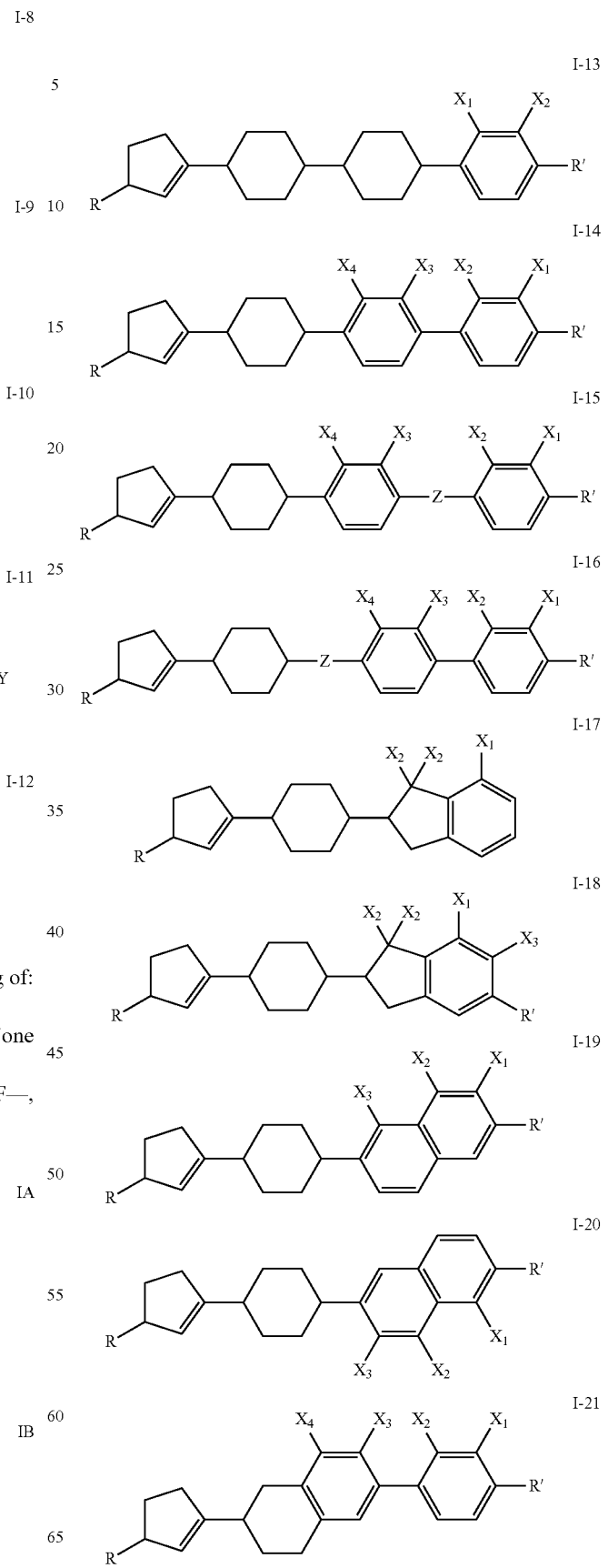

I-22
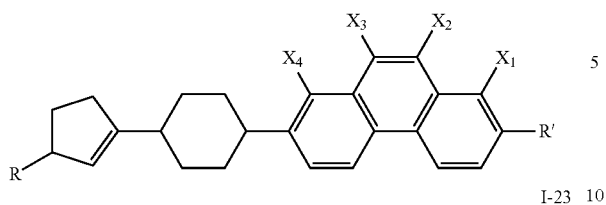
I-25
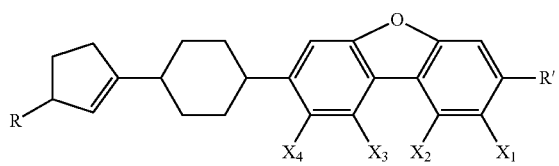
I-23
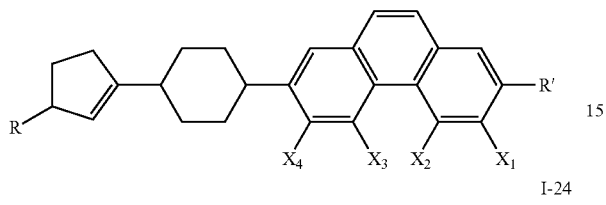
I-24
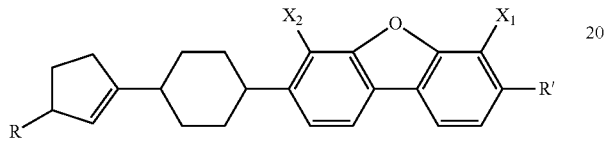
where for formula IA, IB and I-13 to I-25, R is C1-C7 n-alkyl;
R' is C1-C7 alkyl, alkenyl, alkoxy, or alkenyloxy;
X1, X2, X3 and X4 are independently selected from the group consisting of: H, F, Cl, CHF2 and CF3; with the proviso that at least two of X1 to X4 are independently F, Cl, CHF2 or CF3;
Z is independently selected from the group consisting of: —C2H4-, —CF2O—, —CF=CF—, —C2F4-, and —CO2-.
* * * * *

UNITED STATES PATENT AND TRADEMARK OFFICE
CERTIFICATE OF CORRECTION

| | | |
|---|---|---|
| PATENT NO. | : 8,444,877 B2 | Page 1 of 1 |
| APPLICATION NO. | : 12/812198 | |
| DATED | : May 21, 2013 | |
| INVENTOR(S) | : Xinhua Chen and Amaranatha Reddy | |

It is certified that error appears in the above-identified patent and that said Letters Patent is hereby corrected as shown below:

In the Specification:

In column 1, lines 58-65, Formula I, replace "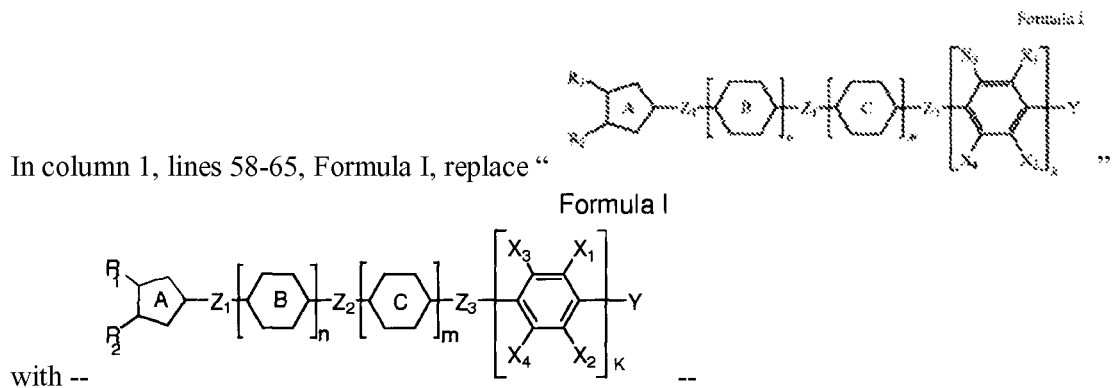"

with --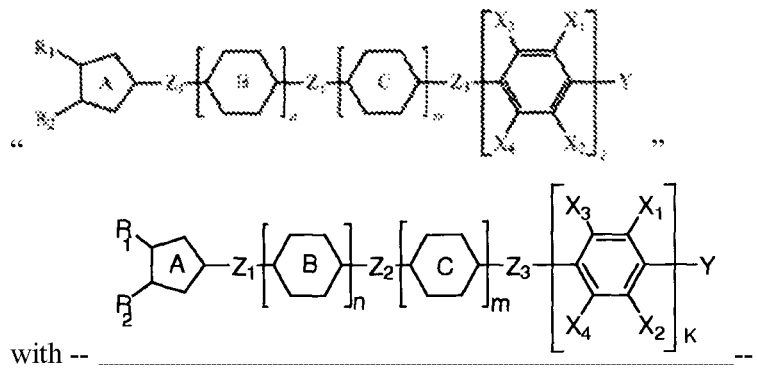--

In the Claims:

In claim 1, column 20, Formula 1 at lines 30-35, replace

"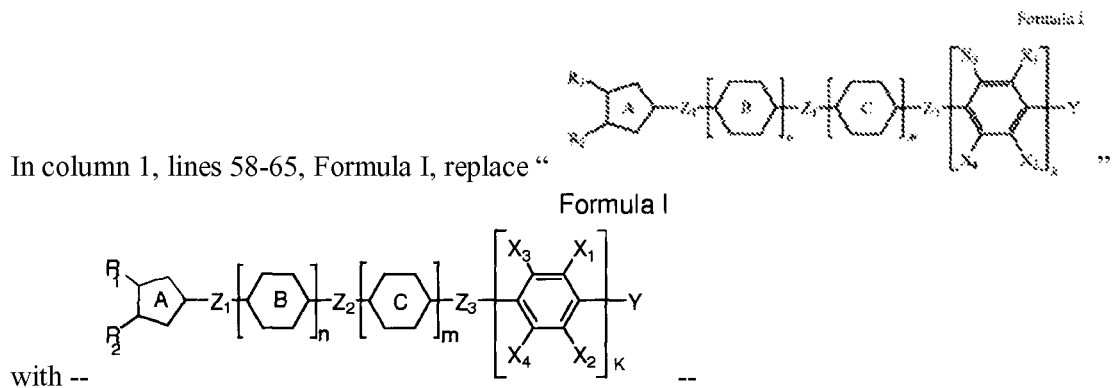"

with --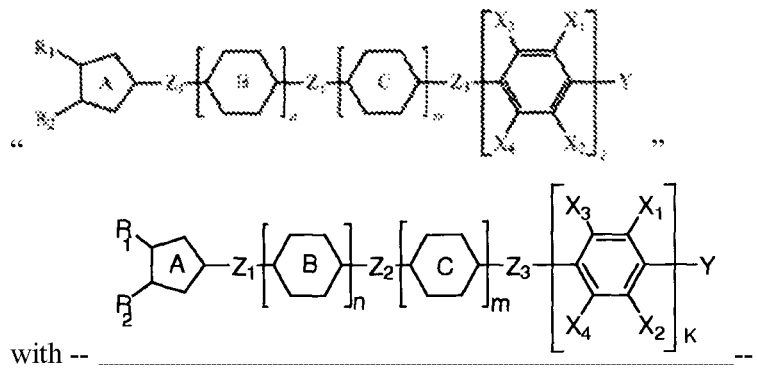--

Signed and Sealed this
Twenty-sixth Day of November, 2013

Margaret A. Focarino
*Commissioner for Patents of the United States Patent and Trademark Office*